United States Patent
Xu et al.

(10) Patent No.: US 10,443,105 B2
(45) Date of Patent: *Oct. 15, 2019

(54) METHODS AND COMPOSITIONS FOR CORRELATING GENETIC MARKERS WITH PROSTATE CANCER RISK

(71) Applicant: Wake Forest University Health Sciences, Winston-Salem, NC (US)

(72) Inventors: Jianfeng Xu, Clemmons, NC (US); Siqun Lilly Zheng, Clemmons, NC (US); Jielin Sun, Oak Ridge, NC (US); Andrew Karim Kader, San Diego, CA (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/675,273

(22) Filed: Aug. 11, 2017

(65) Prior Publication Data

US 2018/0187265 A1 Jul. 5, 2018

Related U.S. Application Data

(62) Division of application No. 13/818,602, filed as application No. PCT/US2011/050337 on Sep. 2, 2011, now Pat. No. 9,732,389.

(60) Provisional application No. 61/379,965, filed on Sep. 3, 2010.

(51) Int. Cl.
*C12Q 1/68* (2018.01)
*C12Q 1/6886* (2018.01)

(52) U.S. Cl.
CPC ..... *C12Q 1/6886* (2013.01); *C12Q 2600/156* (2013.01); *C12Q 2600/172* (2013.01)

(58) Field of Classification Search
None
See application file for complete search history.

(56) References Cited

U.S. PATENT DOCUMENTS

| | | | |
|---|---|---|---|
| 6,306,087 B1 | 10/2001 | Barnhill et al. | |
| 6,316,196 B1 | 11/2001 | Morten | |
| 6,355,427 B1 | 3/2002 | Jupe et al. | |
| 6,581,038 B1 | 6/2003 | Mahran | |
| 6,582,908 B2 | 6/2003 | Fodor et al. | |
| 7,127,355 B2 | 10/2006 | Cox et al. | |
| 7,718,372 B2 | 5/2010 | Cramer et al. | |
| 7,960,109 B2 | 6/2011 | Hessels et al. | |
| 7,998,674 B2 | 8/2011 | Kao et al. | |
| 9,732,389 B2* | 8/2017 | Xu ................. | C12Q 1/6886 |
| 2005/0196770 A1 | 9/2005 | Cox et al. | |
| 2008/0038744 A1 | 2/2008 | Cramer et al. | |
| 2009/0099789 A1 | 4/2009 | Stephan et al. | |
| 2009/0226912 A1 | 9/2009 | Xu et al. | |
| 2009/0298085 A1 | 12/2009 | Gocke et al. | |
| 2009/0299645 A1 | 12/2009 | Colby et al. | |
| 2009/0307179 A1 | 12/2009 | Colby et al. | |
| 2009/0307181 A1 | 12/2009 | Colby et al. | |
| 2009/0317799 A1 | 12/2009 | Amundadottir et al. | |
| 2009/0324559 A1 | 12/2009 | Sakurada et al. | |
| 2010/0041037 A1 | 2/2010 | Gudmundsson et al. | |
| 2010/0042438 A1 | 2/2010 | Moore et al. | |
| 2010/0047782 A1 | 2/2010 | Cotterchio et al. | |
| 2010/0070455 A1 | 3/2010 | Halperin et al. | |
| 2010/0120045 A1 | 5/2010 | Helgadottir et al. | |
| 2010/0129799 A1 | 5/2010 | Gudmundsson al. | |
| 2010/0130526 A1 | 5/2010 | Glinsky | |
| 2012/0150032 A1 | 6/2012 | Gudmundsson et al. | |
| 2012/0178082 A1 | 7/2012 | Xu et al. | |
| 2014/0057795 A1 | 2/2014 | Xu et al. | |
| 2015/0031032 A1 | 1/2015 | Xu | |

FOREIGN PATENT DOCUMENTS

| | | | |
|---|---|---|---|
| WO | WO 2006/123369 A1 | 11/2006 | |
| WO | WPO 2008/050356 A1 | 5/2008 | |
| WO | WO 2009/056862 A2 | 5/2009 | |
| WO | WO 2009/069152 A2 | 6/2009 | |
| WO | WO-2009069152 A2 * | 6/2009 | ........... C12Q 1/6886 |
| WO | WO 2009/085196 A1 | 7/2009 | |
| WO | WO 2009/117122 A2 | 9/2009 | |
| WO | WO 2010/012823 A1 | 2/2010 | |
| WO | WO 2010/139006 A1 | 12/2010 | |
| WO | WO 2012/031207 A2 | 3/2012 | |
| WO | WO 2012/129408 A2 | 9/2012 | |
| WO | WO 2008/096375 A2 | 8/2014 | |
| WO | WO 2014/152950 A1 | 9/2014 | |

OTHER PUBLICATIONS

Kader et al. (The Prostate 69:1195-1205, 2009) (Year: 2009).*
Gudmundsson et al. (Nature Genetics, vol. 41, No. 10, pp. 1122-1126, published online Sep. 20, 2009) (Year: 2009).*
Olanna et al. (Nature Genetics, vol. 41, No. 10, pp. 1058-1060, published online Sep. 20, 2009) (Year: 2009).*
Eeles et al. Nature Genetics, vol. 41, No. 10, pp. 1116-1121 published online Sep. 20, 2009). (Year: 2009).*
Gomella (Current Opinion in Urology: Jan. 2005—vol. 15—Issue 1—p. 29-32) (Year: 2005).*
"Affymetrix® Genome-Wide Human SNP Array 6.0" *Data Sheet* (4 pages) (2007).

(Continued)

*Primary Examiner* — Juliet C Switzer
(74) *Attorney, Agent, or Firm* — Myers Bigel, P.A.

(57) ABSTRACT

The present invention provides methods of assessing an individual subject's risk of developing prostate cancer, comprising: a) analyzing a nucleic acid sample obtained from the subject and determining a genotype for the subject at a plurality of biallelic polymorphic loci, wherein each of said plurality has an associated allele and an unassociated allele, wherein the genotype is selected from the group consisting of homozygous for the associated allele, heterozygous, and homozygous for the unassociated allele; and b) calculating a cumulative relative risk (CRR) for the subject based on the genotype determined in step (a). A CRR of greater than 1.00 identifies a subject as having an increased risk of developing prostate cancer and also can identify a subject who is a candidate for early PSA screening, prostate biopsy and/or chemoprevention.

13 Claims, 6 Drawing Sheets

(56) References Cited

OTHER PUBLICATIONS

Han et al. "Evaluating 17 breast cancer susceptibility loci in the Nashville breast health study" *Breast Cancer* 22:544-551 (2015).
Long et al. "Evaluating Genome-Wide Association Study-Identified Breast Cancer Risk Variants in African-American Women" *PLoS One* 8(4):e58350 (2013).
Michailidou et al. "Large-scale genotyping identifies 41 new loci associated with breast cancer risk" *Nature Genetics* 45(4):353-361 (2013).
Nordström et al. "A Genetic Score Can Identify Men at High Risk for Prostate Cancer Among Men With Prostate-Specific Antigen of 1-3 ng/ml" *European Urology* 65(6):1184-1190 (2014).
Adolfsson et al. "Clinical characteristics and primary treatment of prostate cancer in Sweden between 1996 and 2005" *Scandinavian Journal of Urology and Nephrology* 41:456-477 (2007).
Ahn et al. "Variation in KLK genes, prostate-specific antigen and risk of prostate cancer" *Nature Genetics* 40(9):1032-1034 (2008).
Al Olama et al. "Multiple loci on 8q24 associated with prostate cancer susceptibility" *Nature Genetics* 41(10):1058-1060 (2009).
Al Olama et al. "A meta-analysis of genome-wide association studies to identify prostate cancer susceptibility loci associated with aggressive and non-aggressive disease" *Human Molecular Genetics* 22(2):408-415 (2013).
Aly et al. "Polygenic Risk Score Improves Prostate Cancer Risk Prediction: Results from the Stockholm-1 Cohort Study" *European Urology* 60:21-28 (2011).
Amundadottir et al. "A common variant associated with prostate cancer in European and African populations" *Nature Genetics* 39(6):652-658 (2006).
Andiappan et al. "Evaluating the Transferability of Hapmap SNPs to a Singapore Chinese Population" *BMC Genetics* 11:36 (2010).
Andriole et al. "Mortality Results from a Randomized Prostate-Cancer Screening Trial" *The New England Journal of Medicine* 360:1310-1319 (2009).
Andriole et al. "Effect of Dutasteride on the Risk of Prostate Cancer" *The New England Journal of Medicine* 362(13):1192-1202 (2010).
Ankerst et al. "Predicting Prostate Cancer Risk Through Incorporation of Prostate Cancer Gene 3" *The Journal of Urology* 180:1303-1308 (2008).
Ankerst et al. "Evaluating the PCPT risk calculator in ten international biopsy cohorts: results from the Prostate Biopsy Collaborative Group" *World Journal of Urology* 30:181-187 (2012).
Björk et al. "Comparison of Analysis of the Different Prostate-Specific Antigen Forms in Serum for Detection of Clinically Localized Prostate Cancer Urology" *Urology* 48:882-888 (1996).
Brawley, Otis W. "Trends in Prostate Cancer in the United States" *Journal of the National Cancer Institute Monographs* 45:152-156 (2012).
Bussemakers et al. "DD3: A New Prostate-specific Gene, Highly Overexpressed in Prostate Cancer" *Cancer Research* 59:5975-5979 (1999).
Cao et al, "MicroRNA-101 negatively regulates Ezh2 and its expression is modulated by androgen receptor and HIF-1α/HIF-1β" *Molecular Cancer* 9(108):1-12 (2010).
Catalona et al. "Use of the Percentage of Free Prostate-Specific Antigen to Enhance Differentiation of Prostate Cancer From Benign Prostatic Disease" *Journal of the American Medical Association* 279(19):1542-1547 (1998).
Chae et al. "Genetic Polymorphisms of Estrogen Receptors αand βand the Risk of Developing Prostate Cancer" *PLoS ONE* 4(8):e6523 (2009).
Chang et al. "Genome-Wide Screen for Prostate Cancer Susceptibility Genes in Men With Clinically Significant Disease" *The Prostate* 64:356-361 (2005).
Chang et al. "Two-Locus Genome-Wide Linkage Scan for Prostate Cancer Susceptibility Genes With an Interaction Effect" *Hum. Genet.* 118:716-724 (2005).
Chang et al. "Integration of Somatic Deletion Analysis of Prostate Cancers and Germline Linkage Analysis of Prostate Cancer Families Reveals Two Small Consensus Regions for Prostate Cancer Genes at 8p" *Cancer Res.* 67(9):4098-4103 (2007).
Chang et al. "Fine mapping association study and functional analysis implicate a SNP in MSMB at 10q11 as a causal variant for prostate cancer risk" *Human Molecular Genetics* 18(7):1368-1375 (2009).
Chen et al, "A Genetic Risk Score Combining Ten Psoriasis Risk Loci Improves Disease Prediction" *PLoS ONE* 6(4):e19454 (2011).
Cheng et al."8q24 and prostate cancer: association with advanced disease and meta-analysis" *European Journal of Human Genetics* 16:496-505 (2008).
Cheng et al. "Genetic and Epigenetic Inactivation of TNFRSF10C in Human Prostate Cancer" *The Prostate* 69:327-335 (2009).
Christensen et al. "Genome-Wide Linkage Analysis of 1,233 Prostate Cancer Pedigrees From the International Consortium for Prostate Cancer Genetics Using Novel sumLINK and sumLOD Analyses" *The Prostate* 70:735-744 (2010).
Christensson et al. "Enzymatic activity of prostate-specific antigen and its reactions with extracellular serine proteinase inhibitors" *European Journal of Biochemistry* 194:755-763 (1990).
Cooperberg et al. "Risk Assessment for Prostate Cancer Metastasis and Mortality at the Time of Diagnosis" *J Natl. Cancer Inst.* 101:878-887 (2009).
Cullen et al. "The burden of prostate cancer in Asian nations" *Journal of Carcinogenesis* 11(7):61-69 (2012).
De Kok et al. "$DD3^{PCA3}$, a Very Sensitive and Specific Marker to Detect Prostate Tumors" *Cancer Research* 62:2695-2698 (2002).
DeLong et al. "Comparing the Areas Under Two or More Correlated Receiver Operating Characteristic Curves: A Nonparametric Approach" *Biometrics* 44:837-845 (1988).
Deras et al. "PCA3: A Molecular Urine Assay for Predicting Prostate Biopsy Outcome" *The Journal of Urology* 179:1587-1592 (2008).
Dianat et al. "Gene Polymorphisms and Prostate Cancer: the Evidence" *Journal Compilation* 104:1560-1572 (2009).
Djavan et al. "Optimal Predictors of Prostate Cancer on Repeat Prostate Biopsy: A Prospective Study of 1,051 Men" *The Journal of Urology* 163:1144-1149 (2000).
Duggan et al. "Two Genome-wide Association Studies of Aggressive Prostate Cancer implicate Putative Prostate Tumor Suppressor Gene DAB21P" *J Natl. Cancer Inst.* 99:1836-1844 (2007).
Easton et al. "Genome-wide association studies in cancer" *Human Molecular Genetics* 17(2):R109-R115 (2008).
Eeles et al. "Multiple newly identified loci associated with prostate cancer susceptibility" *Nature Genetics* 40(3):316-321 (2008).
Eeles et al. "Identification of seven new prostate cancer susceptibility loci through a genome-wide association study" *Nature Genetics* 41(10):1116-1123 (2009).
Epstein et al. "The 2005 International Society of Urological Pathology (ISUP) Consensus Conference on Gleason Grading of Prostatic Carcinoma" *Am J Surg. Pathol.* 29(9):1228-1242 (2005).
European Search Report Corresponding to European Patent Application No. 11 822 720.6 (7 Pages) (dated Jan. 9, 2014).
Farkas et al. "National Trends in the Epidemiology of Prostate Cancer, 1973 to 1994: Evidence for the Effectiveness of Prostate-Specific Antigen Screening" *Urology* 52(3):444-448 (1998).
Ferlay et al. "Estimates of worldwide burden of cancer in 2008: GLOBOCAN 2008" *International Journal of Cancer* 127:2893-2917 (2010).
Filella et al. "Evaluation of [-2] proPSA and Prostate Health Index (phi) for the detection of prostate cancer: a systematic review and meta-analysis" *Clinical Chemistry and Laboratory Medicine* 51(4):729-739 (2013).
Fitzgerald et al "Analysis of Recently Identified Prostate Cancer Susceptibility Loci in a Population-based Study: Associations with Family History and Clinical Features" *Clin Cancer Res.* 15:3231-3237 (2009).
Freedman et al. "Admixture mapping identifies 8q24 as a prostate cancer risk locus in African-American men" *PNAS* 103(38):14068-14073 (2006).
Gelmann et al. "Complexities of Prostate-Cancer Risk" *New England Journal of Medicine* 358(9):961-963 (2008).

(56) References Cited

OTHER PUBLICATIONS

Grönberg "Prostate Cancer Epidemiology" *The Lancet* 361:859-864 (2003).
Groskopf et al. "APTIMA PCA3 Molecular Urine Test: Development of a Method to Aid in the Diagnosis of Prostate Cancer" *Clinical Chemistry* 52(6):1089-1095 (2006).
Gsur et al. "Polymorphic CAG repeats in the androgen receptor gene, prostate-specific antigen polymorphism and prostate cancer risk" *Carcinogenesis* 23(10):1647-1651 (2002).
Gudmundsson et al. "Genome-wide association study identifies a second prostate cancer susceptibility variant at 8q24" *Nature Genetics* 39(5):631-637 (2007).
Gudmundsson et al. "Two variants on chromosome 17 confer prostate cancer risk, and the one in TCF2 protects against type 2 diabetes" *Nature Genetics* 39(8):977-983 (2007).
Gudmundsson et al. "Common sequence variants on 2p15 and Xp11.22 confer susceptibility to prostate cancer" *Nature Genetics* 40(3):281-283 (2008).
Gudmundsson et al. "Genome-wide association and replication studies identify four variants associated with prostate cancer susceptibility" *Nature Genetics* 41(10):1122-1128 (2009).
Haiman et al. "Multiple regions within 8q24 independently affect risk for prostate cancer" *Nature Genetics* 39(5):638-644 (2007).
Helfand et al. "Tumor Characteristics of Carriers and Noncarriers of the decode 8q24 Prostate Cancer Susceptibility Alleles" *The Journal of Urology* 179:2197-2202 (2008).
Hoedemaeker et al. "Staging Prostate Cancer" *Microscopy Research and Technique* 51:423-429 (2009).
Hsu et al. "A Multigenic Approach to Evaluating Prostate Cancer Risk in a Systematic Replication Study" *Cancer Genetics and Cytogenetics* 183:94-98 (2008).
Hsu et al. "A Novel Prostate Cancer Susceptibility Locus at 19q13" *Cancer Research* 69(7):2720-2723 (2009).
Hsu et al. "Comparison of two methods for estimating absolute risk of prostate cancer based on SNPs and family history" *Cancer Epidemiol. Biomarkers Prev.* 19(4):1083-1088 (2010).
Hunter et al. "Drinking From the Fire Hose—Statistical Issues in Genomewide Association Studies" *N. Engl. J. Med.* 357(5):436-439 (2007).
International Preliminary Report on Patentability corresponding to International Application No. PCT/US2008/013874 (9 pages) (dated Jul. 1, 2010).
International Preliminary Report on Patentability corresponding to International Application No. PCT/US2011/050337 (7 pages) (dated Mar. 14, 2013).
International Search Report and the Written Opinion of the International Searching Authority corresponding to International Application No. PCT/US08/13874 (13 pages) (dated Apr. 14, 2009).
International Search Report and the Written Opinion of the International Searching Authority corresponding to International Application No. PCT/US2011/050337 (12 pages) (dated Apr. 26, 2012).
International Search Report and the Written Opinion of the International Searching Authority corresponding to International Application No. PCT/US2014/028371 (15 pages) (dated Jul. 22, 2014).
International Search Report and the Written Opinion of the International Searching Authority corresponding to International Application No. PCT/US2015/055558 (13 pages) (dated Dec. 21, 2015).
Ippolito et al. "An integrated functional genomics and metabolomics approach for defining poor prognosis in human neuroendocrine cancers" *Proceedings of the National Academy of Sciences* 102(28):9901-9906 (2005).
Janssens et al. "The impact of genotype frequencies on the clinical validity of genomic profiling for predicting common chronic diseases" *Genetics in Medicine* 9(8):528-535 (2007).
Jemal et al. "Cancer Statistics, 2007" *CA Cancer J. Clin.* 57(1):43-66 (2007).
Jemal et al. "Cancer Statistics, 2009" *CA Cancer J Clin.* 59:225-249 (2009).
Jemal et al. "Global Cancer Statistics" *CA: A Cancer Journal for Clinicians* 61:69-90 (2011).
Jiang et al. "Prediction of Prostate Cancer From Prostate Biopsy in Chinese Men Using a Genetic Score Derived From 24 Prostate Cancer Risk-Associated SNPs" *Prostate* 73(15):1651-1659 (2013).
Jin et al. "Genome-wide copy-number variation analysis identifies common genetic variants at 20p13 associated with aggressiveness of prostate cancer" *Carcinogenesis* 32:1057-1062 (2011).
Johns et al. "A Systematic Review and Meta-Analysis of Familial Prostate Cancer Risk" *BJU International* 91:789-794 (2003).
Kader et al. "Individual and cumulative Effect of Prostate Cancer Risk-Associated Variants on Clinicopathologic Variables in 5,895 Prostate Cancer Patients" *The Prostate* 69:1195-1205 (2009).
Kader et al. "Potential Impact of Adding Genetic Markers to Clinical Parameters in Predicting Prostate Biopsy Outcomes in Men Following an Initial Negative Biopsy: Findings from the REDUCE Trial" *European Urology* 62(6):953-961 (2012).
Karlson et al. "Cumulative Association of Twenty-Two Genetic Variants with Seropositive Rheumatoid Arthritis Risk" *Annals of the Rheumatic Diseases* 69(6):1077-1085 (2010).
Karlsson et al. "A Population-based Assessment of Germline HOXB13 G84E Mutation and Prostate Cancer Risk" *European Urology* 65:169-176 (2014).
Kattan et al. "A Preoperative Nomogram for Disease Recurrence Following Radical Prostatectomy for Prostate Cancer" *Journal of the National Cancer Institute* 90(10):766-771 (1998).
Kim et al. "Integrative Analysis of Genomic Aberrations Associated with Prostate Cancer Progression" *Cancer Research* 67:8229-8239 (2007).
Kim et al. "Genetic and Epigenetic Inactivation of LPL Gene in Human Prostate Cancer" *Int. J. Cancer* 124:734-738 (2009).
Kim et al. "Prostate cancer risk-associated variants reported from genome-wide association studies: meta-analysis and their contribution to genetic variation" *Prostate* 70(16):1729-1738 (2010).
Knowles "Role of FGFR3 in urothelial cell carcinoma: biomarker and potential therapeutic target" *World Journal of Urology* 25:581-593 (2007).
Kote-Jarai et al. "Multiple Novel Prostate Cancer Predisposition Loci Confirmed by an International Study: The Practical Consortium" *Cancer Epidemiol. Biomarkers Prev.* 17:2052-2061 (2008).
Kraft et al. "Genetic Risk Prediction—Are We There Yet?" *The New England Journal of Medicine* 360(17):1701-1703 (2009).
Langdahl et al. "Osteoporotic Fractures are Associated with an 86-Repeat Base Pair Polymorphism in the Interleukin-1-Receptor Antagonist Gene but not with Polymorphisms in the Interleukin-1βGene" *Journal of Bone and Mineral Research* 15(3):402-414 (2000).
Lange et al. "Family-Based Samples Can Play an Important Role in Genetic Association Studies" *Cancer Epidemiol Biomarkers Prev* 17(9):2208-2214 (2008).
Lange et al. "Fine-Mapping the Putative Chromosome 17q21-22 Prostate Cancer Susceptibility Gene to a 10 cM Region Based on Linkage Analysis" *Hum Genet.* 121:49-55 (2007).
Levin et al. "Chromosome 17q12 Variants Contribute to Risk of Early-Onset Prostate Cancer" *Cancer Res* 68(16):6492-6495 (2008).
Leyten et al. "Prospective Multicentre Evaluation of PCA3 and TMPRSS2-ERG Gene Fusions as Diagnostic and Prognostic Urinary Biomarkers for Prostate Cancer" *European Urology* 65:534-542 (2014).
Lichtenstein et al. "Environmental and Heritable Factors in the Causation of Cancer: Analyses of Cohorts of Twins from Sweden, Denmark, and Finland" *The New England Journal of Medicine* 343(2):78-85 (2000).
Lin "Functions of heparin sulfate proteoglycans in cell signaling during development" *Development* 131:6009-6021 (2004).
Lindmark et al. "Interleukin-1 Receptor Antagonist Haplotype Associated With Prostate Cancer Risk" *British Journal of Cancer* 93:493-497 (2005).
Lindström et al. "Comprehensive Genetic Evaluation of Common E-Cadherin Sequence Variants and Prostate Cancer Risk: Strong Confirmation of Functional Promoter SNP" *Hum. Genet.* 118:339-347 (2005).
Lindström et al. "Familial concordance in cancer survival: a Swedish population-based study" *Lancet Oncol.* 8:1001-06 (2007).

(56) References Cited

OTHER PUBLICATIONS

Lindström et al. "Germ-Line Genetic Variation in the Key Androgen-Regulating Genes Androgen Receptor, Cytochrome P450, and Steriod-5-α-Reductase Type 2 is Important for Prostate Cancer Development" *Cancer Res.* 66(22):11077-11083 (2006).
Lindström et al. "Systematic Replication Study of Reported Genetic Associations in Prostate Cancer: Strong Support for Genetic Variation in the Androgen Pathway" *The Prostate* 66:1729-1743 (2006).
Liu et al. "Comprehensive Assessment of DNA Copy Number Alterations in Human Prostate Cancers Using Affymetrix 100K SNP Mapping Array" *Genes, Chromosomes & Cancer* 45:1018-1032 (2006).
Liu et al. "Deletion of a Small Consensus Region at 6q15, Including the MAP3K7 Gene, is Significantly Associated with High-Grade Prostate Cancers" *Human Cancer Biology* 13(17):5028-5033 (2007).
Liu et al. "Germline Copy Number Polymorphisms Involving Larger Than 100 kb Are Uncommon in Normal Subjects" *The Prostate* 67:227-233 (2007).
Liu et al. "Multiple Genomic Alterations on 21q22 Predict Various TMPRSS2/ERG Fusion Transcripts in Human Prostate Cancers" *Genes, Chromosomes & Cancer* 46:972-980 (2007).
Liu et al. "Homozygous Deletions and Recurrent Amplifications Implicate New Genes Involved in Prostate Cancer" *Neoplasia* 10(8):897-907 (2008).
Liu et al. "Association of a Germ-Line Copy Number Variation at 2p24.3 and Risk for Aggressive Prostate Cancer" *Cancer Res* 69(6):2176-2179 (2009).
Liu et al. "Genetic Markers Associated With Early Cancer-Specific Mortality Following Prostatectomy" *Cancer* 119(13):2405-2412 (2013).
Liu et al. "Somatic DNA copy number alterations and their potential clinical utility for predicting lethal prostate cancer" *Asian Journal of Andrology* 15:586-587 (2013).
Liyanarachchi et al. "Cumulative Risk Impact of Five Genetic Variants Associated with Papillary Thyroid Carcinoma" *Thyroid* 23(12):1532-1540 (2013).
Loeb et al. "Prospective, Multi-Center Evaluation of the Beckman Coulter Prostate Health Index Using WHO Calibration" *The Journal of Urology* 189(5):1702-1706 (2013).
Lotan et al. "Gleason grading of prostatic adenocarcinoma with glomeruloid features on needle biopsy" *Human Pathology* 40:471-477 (2009).
Lu et al. "Association of prostate cancer risk with SNPs in regions containing androgen receptor binding sites captures by ChIP-on-chip analyses" *The Prostate* 72(4):376-385 (2012).
Lu et al. "Chromosomes 4 and 8 Implicated in a Genome Wide SNP Linkage Scan of 762 Prostate Cancer Families Collected by the ICPCG" *Prostate* 72(4):410-426 (2012).
Luderer et al. "Measurement of the Proportion of Free to Total Prostate-Specific Antigen Improves Diagnostic Performance of Prostate-Specific Antigen in the Diagnostic Gray Zone of Total Prostate-Specific Antigen" *Urology* 46(2):187-194 (1995).
Manolio, Teri A. "Cohort studies and the genetics of complex disease" *Nature Genetics* 41(1):5-6 (2009).
Marks et al. "PCA3 Molecular Urine Assay for Prostate Cancer in Men Undergoing Repeat Biopsy" *Urology* 69(3):532-535 (2007).
Mitka, Mike "Is PSA Testing Still Useful?" *JAMA* 292(19):2326-2327 (2004).
Nam et al. "A genome-wide association screen identifies regions on chromosomes 1q25 and 7p21 as risk loci for sporadic prostate cancer" *Prostate Cancer and Prostatic Diseases* 11:241-246 (2008).
Nassir et al. "An ancestry informative marker set for determining continental origin: validation and extension using human genome diversity panels" *BMC Genetics* 10(39):1-13 (2009).
Newcombe et al. "A Comparison of Bayesian and Frequentist Approaches to Incorporating External Information for the Prediction of Prostate Cancer Risk" *Genetic Epidemiology* 36(1):71-83 (2012).

Park et al. "Potential Usefulness of Single Nucleotide Polymorphisms to Identify Persons at High Cancer Risk: An Evaluation of Seven Common Cancers" *Journal of Clinical Oncology* 30(17):2157-2162 (2012).
Peltonen et al. "Dissecting Human Disease in the Postgenomic Era", *Science* 291:1224-1229 (2001).
Pencina et al. "Evaluating the added predictive ability of a new marker: From area under the ROC curve to reclassification and beyond" *Statistics in Medicine* 27:157-172 (2008).
Pharoah et al. "Polygenic susceptibility to breast cancer and implications for prevention" *Nature Genetics* 31:33-36 (2002).
Pharoah et al. "Polygenes, Risk Prediction, and Targeted Prevention of Breast Cancer" *The New England Journal of Medicine* 358(26):2796-2803 (2008).
Presti, Joseph C. "Repeat prostate biopsy—when, where, and how" *Urologic Oncology: Seminars and Original Investigations* 27:312-314 (2009).
Prestigiacomo et al. "A Comparison of the Free Fraction of Serum Prostate Specific Antigen in Men with Benign and Cancerous Prostates: The Best Case Scenario" *The Journal of Urology* 156:350-354 (1996).
Price et al. "Principal components analysis corrects for stratification in genome-wide association studies" *Nature Genetics* 38(8):904-909 (2006).
Prokunina-Olsson et al. "Refining the Prostate Cancer Genetic Association within the JAZF1 Gene on Chromosome 7p15.2" *Cancer Epidemiology, Biomarkers & Prevention* 19(5):1349-1355 (2010).
"Prostate Cancer in Men with Very Low PSA", p. 12 in *Prostate Cancer Discovery, The Brady Urological Institute, Johns Hopkins Medicine* vol. 2:1-20 (Autumn 2005).
Ren et al. "Plateau Effect of Prostate Cancer Risk-Associated SNPs in Discriminating Prostate Biopsy Outcomes" *Prostate* 73(16):1824-1835 (2013).
Robbins et al. "Confirmation Study of Prostate Cancer Risk Variants at 8q24 in African Americans Identifies a Novel Risk Locus" *Genome Research* 17:1717-1722 (2007).
Rosario et al. "Short term outcomes of prostate biopsy in men tested for cancer by prostate specific antigen: prospective evaluation within ProtecT study" *British Medical Journal* 344:1-12 (2012).
Salami et al. "Combining Urinary Detection of TMPRSS2:ERG and PCA3 with Serum PSA to Predict Diagnosis of Prostate Cancer" *Urologic Oncology* 31(5):566-571 (2013).
Salinas et al. "Clinical Utility of Five Genetic Variants for Predicting Prostate Cancer Risk and Mortality" *Prostate* 69(4):363-372 (2009).
Schaid et al. "Pooled genome linkage scan of aggressive prostate cancer: Results from the International Consortium for Prostate Cancer Genetics" *Hum Genet.* 120:471-485 (2006).
Schröder et al. "Screening and Prostate-Cancer Mortality in a Randomized European Study" *The New England Journal of Medicine* 360:13:1320-1328 (2009).
Schumacher et al. "A Common 8q24 Variant in Prostate and Breast Cancer From a Large Nested Case-Control Study" *Cancer Res.* 67(7):2951-2956 (2007).
Severi et al. "The Common Variant rs1447295 on Chromosome 8q24 and Prostate Cancer Risk: Results From an Australian Population-Based Case-Control Study" *Cancer Epidemiol. Biomarkers Prev.* 16(3):610-612 (2007).
Sobti et al. "Role of Hormonal Genes and Risk of Prostate Cancer: Gene-Gene Interactions in a North Indian Population" *Cancer Genetics and Cytogenetics* 185:78-85 (2008).
Sokoll et al. "Proenzyme PSA for the Early Detection of Prostate Cancer in the 2.5-4.0 ng/mL Total PSA Range: Preliminary Analysis" *Urology* 61:274-276 (2003).
Sokoll et al. "A multicenter evaluation of the PCA3 molecular urine test: Pre-analytical effects, analytical performance, and diagnostic accuracy" *Clinica Chimica Acta* 389:1-6 (2008).
Sotos et al. "The Transivity Misconception of Pearson's Correlation Coefficient" *Statistics Education Research Journal* 8(2):33-55 (2009).
Ss74916614 for rs7215323, dbSNP, NCBI, NLM (2007).
Ss75869428 for rs4054823, dbSNP, NCBI, NLM (2007).

(56) References Cited

OTHER PUBLICATIONS

Stattin et al. "Surveillance and Deferred Treatment for Localized Prostate Cancer. Population Based Study in the National Prostate Cancer Register of Sweden" *The Journal of Urology* 180:2423-2430 (2008).
Stephenson et al. "Prostate Cancer-Specific Mortality After Radical Prostatectomy for Patients Treated in the Prostate-Specific Antigen Era" *J Clin Oncol.* 27:4300-4305 (2009).
Sun et al. "Interactions of Sequence Variants in Interleukin-1 Receptor-Associated Kinase4 and the Toll-Like Receptor 6-1-10 Gene Cluster Increase Prostate Cancer Risk" *Cancer Epidemiol. Biomarkers Prev.* 15(3):480-485 (2006).
Sun et al. "Meta-Analysis of Association of Rare Mutations and Common Sequence Variants in the MSRI Gene and Prostate Cancer Risk" *The Prostate* 66:728-737 (2006).
Sun et al. "DNA Copy Number Alterations in Prostate Cancers: A Combined Analysis of Published CGH Studies" *The Prostate* 67:692-700 (2007).
Sun et al. "Association Between Sequence Variants at 17q12 and 17q24.3 and Prostate Cancer Risk in European and African Americans" *The Prostate* 68:691-697 (2008).
Sun et al. "Chromosome 8q24 Risk Variants in Hereditary and Non-Hereditary Prostate Cancer Patients" *The Prostate* 68:489-497 (2008).
Sun et al. "Clinical utility of inherited markers in determining need for repeat biopsy: results from placebo arm of the REDUCE®study" Abstract submitted for ASHG Meeting held in Washington, DC (1 page) (Nov. 2-6, 2010).
Sun et al. "Cumulative Effect of Five Genetic Variants on Prostate Cancer Risk in Multiple Study Populations" *The Prostate* 68:1257-1262 (2008).
Sun et al. "Evidence for two independent prostate cancer risk-associated loci in the HNF1B gene at 17q12" *Nature Genetics* 40(10):1153-1155 (2008).
Sun et al. "Sequence Variants at 22q13 Are Associated With Prostate Cancer Risk" *Cancer Res* 69(1):10-15 (2009).
Sun et al. "Inherited genetic markers discovered to date are able to identify a significant number of men at considerably elevated risk for prostate cancer" *Prostate* 28 71(4):421-430 (2010).
Sun et al. "Genetic Score Is an Objective and Better Measurement of Inherited Risk of Prostate Cancer than Family History" *European Urology* 63(3):585-587 (2013).
Suuriniemi et al. "Confirmation of a Positive Association Between Prostate Cancer Risk and a Locus at Chromosome 8q24" *Cancer Epidemiol. Biomarkers Prev.* 16(4):809-814 (2007).
Terwilliger et al. "An Utter Refutation of the 'Fundamental Theorem of the HapMap'" *European Journal of Human Genetics* 14:426-437 (2006).
Thomas et al. "Multiple loci identified in a genome-wide association study of prostate cancer" *Nature Genetics* 40(3):310-315 (2008).
Thompson et al. "Assessing Prostate Cancer Risk: Results from the Prostate Cancer Prevention Trial" *Journal of the National Cancer Institute* 98(8):529-534 (2006).
Thompson et al. "The Performance of Prostate Specific Antigen for Predicting Prostate Cancer is Maintained After a Prior Negative Prostate Biopsy" *The Journal of Urology* 180:544-547 (2008).
Tomlins et al. "Urine TMPRSS2:ERG Fusion Transcript Stratifies Prostate Cancer Risk in Men with Elevated Serum PSA" *Science Translational Medicine* 3(94):1-12 (2011).
Turner et al. "Utility of Genome-Wide Association Study findings: prostate cancer as a translational research paradigm" *Journal of Internal Medicine* 271(4):344-352 (2012).
Van Gils et al. "The Time-Resolved Fluorescence-Based PCA3 Test on Urinary Sediments after Digital Rectal Examination; a Dutch Multicenter Validation of the Diagnostic Performance" *Clinical Cancer Research* 13(3):939-943 (2007).
Vickers et al. "Decision curve analysis: a novel method for evaluating prediction models" *Medical Decision Making* 26(6):565-574 (2006).

Wacholder et al. "Performance of Common Genetic Variants in Breast-Cancer Risk Models" *The New England Journal of Medicine* 362(11):986-993 (2010).
Wall et al. "Haplotype Blocks and Linkage Disequilibrium in the Human Genome" *Nature Reviews Genetics* 4:587-597 (2003).
Wang et al. "Two Common Chromosome 8q24 Variants Are Associated With Increased Risk for Prostate Cancer" *Cancer Res* 67(7):2944-2950 (2007).
Waters et al. "Generalizability of Associations from Prostate Cancer GWAS in Multiple Populations" *Cancer Epidemiology, Biomarkers & Prevention* 18(4):1285-1289 (2009).
Wiklund et al. "Association of Reported Prostate Cancer Risk Alleles With PSA Levels Among Men Without a Diagnosis of Prostate Cancer" *The Prostate* 69:419-427 (2009).
Wiklund et al. "Established Prostate Cancer Susceptibility Variants are not Associated with Disease Outcome" *Cancer Epidemiol. Biomarkers Prev.* 18:1659-1662 (2009).
Witte "Multiple prostate cancer risk variants on 8q24", *Nature Genetics* 39(5):579-580 (2007).
Witte et al. "Prostate cancer genomics: towards a new understanding" *Nature Reviews Genetics* 10:77-82 (2009).
Xie et al. "Germ-line sequence variants of PTEN do not have an important role in hereditary and non-hereditary prostate cancer susceptibility" *Journal of Human Genetics* 56(7):496-502 (2011).
Xu et al. "The Interaction of Four Genes in the Inflammation Pathway Significantly Predicts Prostate Cancer Risk" *Cancer Epidemiol. Biomarkers Prev.* 14(11):2563-2568 (2005).
Xu et al. "Germline ATBFI Mutations and Prostate Cancer Risk" *The Prostate* 66:1082-1085 (2006).
Xu et al. "Association of Prostate Cancer Risk Variants With Clinicopathologic Characteristics of the Disease" *Clin Cancer Res* 14(18):5819-5824 (2008).
Xu et al. "Estimation of Absolute Risk for Prostate Cancer using Genetic Markers and Family History" *Prostate* 69(14):1565-1572 (2009).
Xu et al. "Inherited genetic variant predisposes to aggressive but not indolent prostate cancer" *PNAS* 107(5):2136-2140 (2010).
Xu et al. "Prostate cancer risk-associated genetic markers and their potential cinical utility" *Asian Journal of Andrology* 15:314-322 (2013).
Xu, Jianfeng "Public Health Genomics: Genomic-targeted cancer screening" Presentation at the Shanghai Forum (May 25, 2014); Presentation at the International Conference on Frontiers in Chronic Disease Research and Prevention (May 31, 2014) (23 pages).
Xue et al. "Genetic Determinants of Serum Prostate-specific Antigen levels in Healthy Men from a Multiethnic Cohort" *Cancer Epidemiology, Biomarkers & Prevention* 10:575-579 (2001).
Yanke et al. "Validation of a Nomogram for Predicting Positive Repeat Biopsy for Prostate Cancer" *The Journal of Urology* 173:421-424 (2005).
Yeager et al. "Genome-wide association study of prostate cancer identifies a second risk locus at 8q24" *Nature Genetics* 39(5):645-649 (2007).
Yeager et al. "Identification of a new prostate cancer susceptibility locus on chromosome 8q24" *Nature Genetics* 41(10):1055-1057 (2009).
Zabaleta et al. "Interactions of Cytokine Gene Polymorphisms in Prostate Cancer Risk" *Carcinogenesis* 29(3):573-578 (2008).
Zafarana et al. "Copy Number Alterations of c-MYC and PTEN Are Prognostic Factors for Relapse After Prostate Cancer Radiotherapy" *Cancer* 118:4053-4062 (2012).
Zheng et al. "A Comprehensive Association Study for Genes in Inflammation Pathway Provides Support for Their Roles in Prostate Cancer Risk in the CAPS Study" *The Prostate* 66:1556-1564 (2006).
Zheng et al. "Germ-Line Mutation of NKX3.1 Cosegregates with Hereditary Prostate Cancer and Alters the Homeodomain Structure and Function" *Cancer Res.* 66(1):69-77 (2006).
Zheng et al. "Association Between Two Unlinked Loci at 8q24 and Prostate Cancer Risk Among European Americans" *J Natl. Cancer Inst.* 99:1525-1533 (2007).

(56) References Cited

OTHER PUBLICATIONS

Zheng et al. "Cumulative Association of Five Genetic Variants with Prostate Cancer" *The New England Journal of Medicine* 358(9):910-919 (2008).

Zheng et al. "Cumulative Association of Five Genetic Variants with Prostate Cancer" *N. Engl. J. Med.* 358(9):910-919 (2008); including related correspondence and authors' reply 358(25):2738-2741 (2008).

Zheng et al. "Genetic Variants and Family History Predict Prostate Cancer Similar to Prostate-Specific Antigen" *Clin Cancer Res* 15(3):1105-1111 (2009).

Zheng et al. "Two Independent Prostate Cancer Risk-Associated Loci at 11q13" *Cancer Epidemiol. Biomarkers Prev.* 18(6):1815-1820 (2009).

Affymetrix Mapping 250K Sty2 SNP Array, Database entry in NCBI Gene Expression Omnibus (6 pages) (2006).

Johansson et al. "Comprehensive evaluation of genetic variation in the IGF1 gene and risk of prostate cancer" Int. J. Cancer, 120:539-542 (2006).

Extended European Search Report corresponding to European Application No. 15851169.1, dated Aug. 13, 2018, 17 pages.

Clarke et al, Basic statistical analysis in genetic case-control studies, Nature Protocols, vol. 6, issue 2, 2011, pp. 121-133.

Din et al, Effect of aspirin and NSAIDs on risk and survival from colorectal cancer, Gut, vol. 59, 2010, pp. 1670-1679.

\* cited by examiner

METHODS AND COMPOSITIONS FOR CORRELATING GENETIC MARKERS WITH PROSTATE CANCER RISK

STATEMENT OF PRIORITY

This application is a divisional application of, and claims priority to, U.S. patent application Ser. No. 13/818,602, filed Oct. 24, 2013 and issued as U.S. Pat. No. 9,732,389 on Aug. 15, 2017, which is a 35 U.S.C. § 371 national phase application of International Application Serial No. PCT/US2011/050337, filed Sep. 2, 2011, which claims the benefit, under 35 U.S.C. § 119(e), of U.S. Provisional Patent Application No. 61/379,965, filed Sep. 3, 2010, the entire contents of each of which are incorporated by reference herein.

STATEMENT OF GOVERNMENT SUPPORT

Aspects of the present invention were made with government support under Grant No. CA148463 awarded by the National Cancer Institute. The United States Government has certain rights in the invention.

FIELD OF THE INVENTION

The present invention provides methods and compositions directed to assessing risk of having or developing prostate cancer by analyzing multiple single nucleotide polymorphisms in nucleic acid of a subject.

BACKGROUND OF THE INVENTION

Prostate cancer (PCa) is the most common solid organ malignancy affecting American men and the second leading cause of cancer related death. Approximately one million prostate biopsies are performed yearly in the U.S. The vast majority of these biopsies are performed due to elevated levels of the PCa marker prostate-specific antigen (PSA). However, only a quarter of these biopsies result in a diagnosis of PCa, highlighting the inadequate performance of currently available parameters such as PSA to predict PCa. Persistently elevated PSA levels and/or other clinical parameters that prompted initial biopsies contribute to stress and anxiety among both patients and their urologists. Thus, the predictive performance of currently available clinical parameters such as PSA is limited. Furthermore, management of men following negative prostate biopsy for prostate cancer is challenging. Novel biomarkers are urgently needed to better determine the need for initial and repeat prostate biopsy and assess an individual's risk.

Single nucleotide polymorphisms (SNPs) are stable genetic markers throughout the human genome, which can be tested for their association with various disease traits. These markers can be tested at birth and will not change in a patient's lifetime and thus represent a new form of biomarkers that predict lifetime risk to disease as opposed to an immediate risk.

Numerous PCa risk-associated single nucleotide polymorphisms (SNPs) have been discovered from genome-wide association studies (GWAS). To date, 33 SNPs have been consistently found, in several populations of Caucasian race, to be associated with prostate cancer (PCa) risk (Table 1). These risk-associated SNPs have been consistently replicated in multiple case-control study populations of European descent. Although each of these SNPs is only moderately associated with PCa risk, a genetic score based on a combination of risk-associated SNPs can be used to identify an individual's risk for PCa. These risk-associated SNPs have broad practical applications because they are common in the general population.

The present invention overcomes previous shortcomings in the art by identifying significant statistical associations between multiple genetic markers and prostate cancer risk.

SUMMARY OF THE INVENTION

The present invention provides a method of identifying a subject as having an increased risk of developing prostate cancer, comprising: a) determining, from a nucleic acid sample obtained from the subject, a genotype for the subject at a plurality of biallelic polymorphic loci, wherein each of said plurality has an associated allele and an unassociated allele, wherein the genotype is selected from the group consisting of homozygous for the associated allele, heterozygous, and homozygous for the unassociated allele; and b) calculating a cumulative relative risk (CRR, also known as genetic score) for the subject based on the genotype determined in step (a), wherein a cumulative relative risk of greater than 1.0 identifies the subject as having an increased risk of developing prostate cancer. The step of determining includes manipulating a fluid or tissue sample obtained from the subject to extract nucleic acid of the subject from the sample in a form that allows for the nucleotide sequence of the nucleic acid to be identified.

In the methods of this invention, identification of the subject's increased risk of developing prostate cancer can also includes information about the subject's family history, prostate specific antigen (PSA) level, free to total PSA ratio, age, prostate volume, prior prostate biopsy history, number of previous biopsy cores and/or family history. Such information can, for example, be identified in quantitative terms that can be incorporated into the calculations described herein to determine how these factors influence the subject's risk of developing prostate cancer. Thus, in some embodiments, the subject can have a family history of prostate cancer or the subject may have no family history of prostate cancer. In some embodiments, the subject may have never had a prostate biopsy and in some embodiments, the subject may have had a prior negative prostate biopsy. In further embodiments, the subject may have had a prior positive prostate biopsy.

The methods of this invention have utility in guiding the subject and his clinician in determining courses of action for treating or preventing or monitoring the occurrence of prostate cancer. Thus, in some embodiments, the identification of the subject as having an increased risk of developing prostate cancer identifies the subject as a candidate for prostate serum antigen (PSA) screening prior to age 50. Thus, due to the subject's increased risk of developing prostate cancer, such screening at an early age may allow for the detection of prostate cancer at is onset or at an early stage when it can be readily treated.

In further embodiments, identification of the subject as having an increased risk of developing prostate cancer according to the methods of this invention identifies the subject as a candidate for prostate biopsy. In particular embodiments, a subject with a CRR of greater than 1.00, together with other clinical variables, such as PSA, prostate volume and digital rectal exam (DRE) is a subject who is a good candidate for prostate biopsy. Thus, due to the subject's increased risk of developing prostate cancer, such a biopsy may allow for the detection of prostate cancer at is onset or at an early stage when it can be readily treated.

In yet further embodiments, identification of the subject as having an increased risk of developing prostate cancer according to the methods of this invention identifies a subject who has had a prior negative prostate biopsy as a candidate for a subsequent or repeat biopsy prostate biopsy. Thus, due to the subject's increased risk of developing prostate cancer, such a biopsy may allow for the detection of prostate cancer at is onset or at an early stage when it can be readily treated.

In additional embodiments, identification of the subject as having an increased risk of developing prostate cancer according to the present invention identifies the subject as a candidate for chemopreventive therapy, such as, for example, a 5-alpha reductase inhibitor (e.g., dutasteride; finasteride) as is known in the art. In particular embodiments, a subject with a CRR of greater than 1.00 and/or a positive family history of prostate cancer should be considered for chemoprevention.

In the methods of this invention, the plurality of biallelic polymorphic loci employed in the methods of this invention is a multiplicity (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 or 33), in any combination, of the 33 single nucleotide polymorphisms of Table 1. In some embodiments, the plurality or biallelic polymorphic loci employed in the methods of this invention is the 33 single nucleotide polymorphisms of Table 1.

BRIEF DESCRIPTION OF THE DRAWINGS

FIG. 6, panels a, b and c show the distribution of estimated risk for each of the three models. These models consist of genetic score (GS), GS plus three pre-biopsy variables (GS+3 variables), and GS plus three pre-biopsy and 3 post-biopsy variables (GS+5 variables). FIG. 6, panels d, e and f show that, for each respective model (GS, GS+3, GS+5), the PCa detection rate trends upward in reflection of increasing risk quartile.

DETAILED DESCRIPTION OF THE INVENTION

Figure 1:
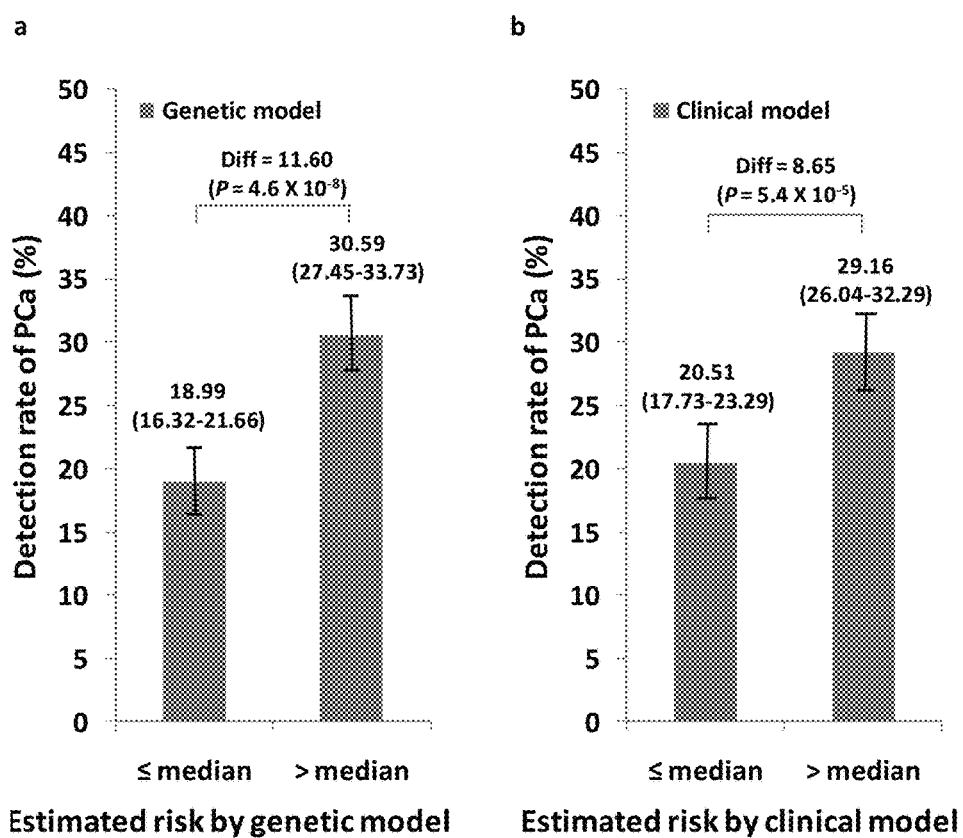
FIG. 1. Detection rates for prostate cancer for men below or above the median estimated risk based on panel a) the genetic model (genetic score of 33 PCa risk-associated SNPs) and panel b) the best clinical model (with five parameters: age, family history, free/total PSA ratio, prostate volume, and number of cores at initial biopsy). Detection rates for the genetic model were directly estimated. Detection rates for the best clinical model were estimated based on four-fold cross validation. Vertical lines in each bar represent 95% CI of detection rates.

The present invention is explained in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure, which do not depart from the instant invention. Hence, the following specification is intended to illustrate some particular embodiments of the invention, and not to exhaustively specify all permutations, combinations and variations thereof.

The present invention is based on the unexpected discovery of a method of predicting PCa risk in an individual, based on an assessment of the individual's genotype at a multiplicity (e.g., any 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 or 33, in any combination) of the 33 SNPs of Table 1. In some embodiments, the method can include an assessment of an individual's genotype at all 33 SNPs of Table 1. In some embodiments, the method can also include an assessment of an individual's genotype at any SNP site in linkage disequilibrium (LD) with any of the 33 SNPs in Table 1. This method, which is called PCS33, provides a powerful predictor of PCa risk. This predictor out-performs any of the currently available parameters of PCa risk as assessed in a unique study population (Table 2). In addition, this predictor can improve the ability of a collection of currently available parameters to predict any PCa risk. Furthermore, this test can be used alone, to identify higher risk individuals who wish to pursue PCa screening or together with established predictors to identify men who may warrant an initial or repeat prostate biopsy. The output of the test can be a cumulative relative risk (CRR, an estimated risk based on the individual's genotype at a multiplicity, in any combination, of these 33 SNPs, which is a relative risk based on genotype with respect to the general population), a percentile risk (risk level in percentile in the distribution of the population risk to PCa), absolute risk (risk of PCa over time), or PCa risk score (probability of being diagnosed with PCa as determined by a logistic regression model). There is no true normal value for this test, which allows for the patient or treating physician to determine the risk level which is clinically meaningful to that particular individual. Risk in the general population can be determined, for example, from such sources as surveillance, epidemiology and end results (SEER) information, available on the internet at http://seer.cancer.gov.

Thus, in one aspect, the present invention provides a method of assessing a subject's risk of having or developing prostate cancer by carrying out an assessment of the subject's genotype at all of the 33 SNP sites or a multiplicity, in any combination, of the 33 SNP sites listed in Table 1 (e.g., a PCS33 risk assessment) according to the methods described herein.

In some embodiments, the PCS33 risk assessment can be used by itself to predict a subject's risk for PCa, which may direct the subject's desire to pursue PCa screening or alter the frequency of PCa screening.

In further embodiments, the PCS33 risk assessment can be used in combination with known clinical variables (prostate specific antigen (PSA), free to total PSA ratio, age, and/or family history) to predict a subject's risk for PCa. This may help urologists and their patients decide whether to pursue prostate biopsy in men who have never had a prior prostate biopsy.

In yet further embodiments, the PCS33 risk assessment can be used in combination with known clinical variables following negative prostate biopsy (prostate volume, number of previous biopsy cores, PSA, free to total PSA ratio, age, and/or family history) to predict a subject's risk for PCa. This may help urologists and their patients decide whether to pursue repeat prostate biopsy in men who have had a prior negative prostate biopsy.

The risk assessment provided to the patient subjects and their treating urologist may include any or all of the following.

1. Cumulative relative risk (CRR) to PCa. The CRR to PCa provided to the subject is derived by obtaining the subject's genotype at the 33 SNPs of Table 1 and may in addition include information on clinical parameters should they be available. For the genetic component of the CRR (CRR), allelic odds ratios (ORs) are obtained from meta-analyses which are then used to determine a relative risk to the general population for a particular genotype at a particular SNP for an individual. The CRR based on 33 SNPs or a multiplicity, in any combination, of the 33 SNPs is then generated by multiplying the relative risks for each of the SNPs for a given individual. This is the genetic component of the CRR to PCa presented to the subject and represents the fold increase in PCa risk compared to the general population. A similar analysis may be performed including the ORs and relative risks for each available clinical parameter based on the outlined study population and then can be used with the genetic component to provide an overall CRR to PCa.

2. Percentile risk to PCa. The percentile risk is generated by determining the risk level in percentile in the distribution of population relative risk for PCa.

3. Absolute risk to PCa. Absolute risk is determined by taking into consideration the CRR and incidence and mortality rates from PCa and mortality due to other causes. This describes the PCa risk over time and for the purposes of this invention, represents the lifetime risk of PCa.

4. PCa risk score. PCa risk score is another means to measure the probability of being diagnosed with PCa. It does not take into consideration time or population parameters such as disease incidence or mortality rates. It is generated by fitting the CRR from the genetic component alone or in combination with other predictors (including genetic score, PSA, F/T PSA ratio, family history of PCa, age), into a logistic regression model.

Definitions

As used herein, "a," "an" or "the" can mean one or more than one. For example, "a" cell can mean a single cell or a multiplicity of cells.

Also as used herein, "and/or" refers to and encompasses any and all possible combinations of one or more of the associated listed items, as well as the lack of combinations when interpreted in the alternative ("or").

Furthermore, the term "about," as used herein when referring to a measurable value such as an amount of a compound or agent of this invention, dose, time, temperature, and the like, is meant to encompass variations of ±20%, +10%, +5%, ±1%, +0.5%, or even ±0.1% of the specified amount.

As used herein, the term "prostate cancer" or "PCa" describes an uncontrolled (malignant) growth of cells originating from the prostate gland, which is located at the base of the urinary bladder and is responsible for helping control urination as well as forming part of the semen. Symptoms of prostate cancer can include, but are not limited to, urinary problems (e.g., not being able to urinate; having a hard time starting or stopping the urine flow; needing to urinate often, especially at night; weak flow of urine; urine flow that starts and stops; pain or burning during urination), difficulty having an erection, blood in the urine and/or semen, and/or frequent pain in the lower back, hips, and/or upper thighs.

As used herein, the term "aggressive prostate cancer" means prostate cancer that is poorly differentiated, having a Gleason grade of 7 or above and an "indolent prostate cancer" having a Gleason grade of 6. The Gleason grading system is the most commonly used method for grading PCa.

All the SNP positions described herein are based on Build 36.

Also as used herein, "linked" describes a region of a chromosome that is shared more frequently in family members or members of a population manifesting a particular phenotype and/or affected by a particular disease or disorder, than would be expected or observed by chance, thereby indicating that the gene or genes or other identified marker(s) within the linked chromosome region contain or are associated with an allele that is correlated with the phenotype and/or presence of a disease or disorder (e.g., aggressive PCa), or with an increased or decreased likelihood of the phenotype and/or of the disease or disorder. Once linkage is established, association studies can be used to narrow the region of interest or to identify the marker (e.g., allele or haplotype) correlated with the phenotype and/or disease or disorder.

Furthermore, as used herein, the term "linkage disequilibrium" or "LD" refers to the occurrence in a population of two or more (e.g., 3, 4, 5, 6, 7, 8, 9, 10, etc.) linked alleles at a frequency higher or lower than expected on the basis of the gene frequencies of the individual genes. Thus, linkage disequilibrium describes a situation where alleles occur together more often than can be accounted for by chance, which indicates that the two or more alleles are physically close on a DNA strand.

The term "genetic marker" or "polymorphism" as used herein refers to a characteristic of a nucleotide sequence (e.g., in a chromosome) that is identifiable due to its variability among different subjects (i.e., the genetic marker or polymorphism can be a single nucleotide polymorphism, a restriction fragment length polymorphism, a microsatellite, a deletion of nucleotides, an addition of nucleotides, a substitution of nucleotides, a repeat or duplication of nucleotides, a translocation of nucleotides, and/or an aberrant or alternate splice site resulting in production of a truncated or extended form of a protein, etc., as would be well known to one of ordinary skill in the art).

A "single nucleotide polymorphism" (SNP) in a nucleotide sequence is a genetic marker that is polymorphic for two (or in some case three or four) alleles. SNPs can be present within a coding sequence of a gene, within noncoding regions of a gene and/or in an intergenic (e.g., intron) region of a gene. A SNP in a coding region in which both forms lead to the same polypeptide sequence is termed synonymous (i.e., a silent mutation) and if a different polypeptide sequence is produced, the alleles of that SNP are non-synonymous. SNPs that are not in protein coding regions can still have effects on gene splicing, transcription factor binding and/or the sequence of non-coding RNA.

The SNP nomenclature provided herein refers to the official Reference SNP (rs) identification number as assigned to each unique SNP by the National Center for Biotechnological Information (NCBI), which is available in the GenBank® database.

In some embodiments, the term genetic marker is also intended to describe a phenotypic effect of an allele or haplotype, including for example, an increased or decreased amount of a messenger RNA, an increased or decreased amount of protein, an increase or decrease in the copy number of a gene, production of a defective protein, tissue or organ, etc., as would be well known to one of ordinary skill in the art.

An "allele" as used herein refers to one of two or more alternative forms of a nucleotide sequence at a given position (locus) on a chromosome. An allele can be a nucleotide present in a nucleotide sequence that makes up the coding sequence of a gene and/or an allele can be a nucleotide in a non-coding region of a gene (e.g., in a genomic sequence). A subject's genotype for a given gene is the set of alleles the subject happens to possess. As noted herein, an individual can be heterozygous or homozygous for any allele of this invention.

Also as used herein, a "haplotype" is a set of alleles on a single chromatid that are statistically associated. It is thought that these associations, and the identification of a few alleles of a haplotype block, can unambiguously identify all other alleles in its region. The term "haplotype" is also commonly used to describe the genetic constitution of individuals with respect to one member of a pair of allelic genes; sets of single alleles or closely linked genes that tend to be inherited together.

The terms "increased risk" and "decreased risk" as used herein define the level of risk that a subject has of developing prostate cancer, as compared to a control subject that does not have the polymorphisms and alleles of this invention in the control subject's nucleic acid.

A sample of this invention can be any sample containing nucleic acid of a subject, as would be well known to one of ordinary skill in the art. Nonlimiting examples of a sample of this invention include a cell, a body fluid, a tissue, biopsy material, a washing, a swabbing, etc., as would be well known in the art.

A subject of this invention is any animal that is susceptible to prostate cancer as defined herein and can include, for example, humans, as well as animal models of prostate cancer (e.g., rats, mice, dogs, nonhuman primates, etc.). In some aspects of this invention, the subject can be Caucasian (e.g., white; European-American; Hispanic), as well as of black African ancestry (e.g., black; African American; African-European; African-Caribbean, etc.) or Asian. In further aspects of this invention, the subject can have a family history of prostate cancer or aggressive prostate cancer (e.g., having at least one first degree relative having or diagnosed with prostate cancer or aggressive prostate cancer) and in some embodiments, the subject does not have a family history of prostate cancer or aggressive prostate cancer. Additionally a subject of this invention can have a diagnosis of prostate cancer in certain embodiments and in other embodiments, a subject of this invention does not have a diagnosis of prostate cancer. In yet further embodiments, the subject of this invention can have an elevated prostate-specific antigen (PSA) level and in other embodiments, the subject of this invention can have a normal or non-elevated PSA level. In some embodiments, the PSA level of the subject may not be known and/or has not been measured.

As used herein, "nucleic acid" encompasses both RNA and DNA, including cDNA, genomic DNA, mRNA, synthetic (e.g., chemically synthesized) DNA and chimeras, fusions and/or hybrids of RNA and DNA. The nucleic acid can be double-stranded or single-stranded. Where single-stranded, the nucleic acid can be a sense strand or an antisense strand. In some embodiments, the nucleic acid can be synthesized using oligonucleotide analogs or derivatives (e.g., inosine or phosphorothioate nucleotides, etc.). Such oligonucleotides can be used, for example, to prepare nucleic acids that have altered base-pairing abilities or increased resistance to nucleases.

An "isolated nucleic acid" is a nucleotide sequence that is not immediately contiguous with nucleotide sequences with which it is immediately contiguous (one on the 5' end and one on the 3' end) in the naturally occurring genome of the organism from which it is derived or in which it is detected or identified. Thus, in one embodiment, an isolated nucleic acid includes some or all of the 5' non-coding (e.g., promoter) sequences that are immediately contiguous to a coding sequence. The term therefore includes, for example, a recombinant DNA that is incorporated into a vector, into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment), independent of other sequences. It also includes a recombinant DNA that is part of a hybrid nucleic acid encoding an additional polypeptide or peptide sequence.

The term "isolated" can refer to a nucleic acid or polypeptide that is substantially free of cellular material, viral material, and/or culture medium (e.g., when produced by recombinant DNA techniques), or chemical precursors or other chemicals (when chemically synthesized). Moreover, an "isolated fragment" is a fragment of a nucleic acid or polypeptide that is not naturally occurring as a fragment and would not be found in the natural state.

The term "oligonucleotide" refers to a nucleic acid sequence of at least about five nucleotides to about 500 nucleotides (e.g. 5, 6, 7, 8, 9, 10, 12, 15, 18, 20, 21, 22, 25, 30, 35, 40, 45, 50, 55, 60, 65, 70, 75, 80, 85, 90, 100, 125, 150, 175, 200, 250, 300, 350, 400, 450 or 500 nucleotides). In some embodiments, for example, an oligonucleotide can be from about 15 nucleotides to about 30 nucleotides, or about 20 nucleotides to about 25 nucleotides, which can be used, for example, as a primer in a polymerase chain reaction (PCR) amplification assay and/or as a probe in a hybridization assay or in a microarray. Oligonucleotides of this invention can be natural or synthetic, e.g., DNA, RNA, PNA, LNA, modified backbones, etc., as are well known in the art.

The present invention further provides fragments of the nucleic acids of this invention, which can be used, for example, as primers and/or probes. Such fragments or oligonucleotides can be detectably labeled or modified, for example, to include and/or incorporate a restriction enzyme cleavage site when employed as a primer in an amplification (e.g., PCR) assay.

The detection of a polymorphism, genetic marker or allele of this invention can be carried out according to various protocols standard in the art and as described herein for analyzing nucleic acid samples and nucleotide sequences, as well as identifying specific nucleotides in a nucleotide sequence.

For example, nucleic acid can be obtained from any suitable sample from the subject that will contain nucleic acid and the nucleic acid can then be prepared and analyzed according to well-established protocols for the presence of genetic markers according to the methods of this invention. In some embodiments, analysis of the nucleic acid can be carried by amplification of the region of interest according to amplification protocols well known in the art (e.g., polymerase chain reaction, ligase chain reaction, strand displacement amplification, transcription-based amplification, self-sustained sequence replication (3 SR), Qβ replicase protocols, nucleic acid sequence-based amplification (NASBA), repair chain reaction (RCR) and boomerang DNA amplification (BDA), etc.). The amplification product can then be visualized directly in a gel by staining or the product can be detected by hybridization with a detectable probe. When amplification conditions allow for amplification of all allelic types of a genetic marker, the types can be distinguished by a variety of well-known methods, such as hybridization with an allele-specific probe, secondary amplification with allele-specific primers, by restriction endonuclease digestion, and/or by electrophoresis. Thus, the present invention further provides oligonucleotides for use as primers and/or probes for detecting and/or identifying genetic markers according to the methods of this invention.

In some embodiments, detection of an allele or combination of alleles of this invention can be carried out by an amplification reaction and single base extension. In particular embodiments, the product of the amplification reaction and single base extension is spotted on a silicone chip.

In yet additional embodiments, detection of an allele or combination of alleles of this invention can be carried out by matrix-assisted laser desorption/ionization-time of flight mass spectrometry (MALDI-TOF-MS).

It is further contemplated that the detection of an allele or combination of alleles of this invention can be carried out by various methods that are well known in the art, including, but not limited to nucleic acid sequencing, hybridization assay, restriction endonuclease digestion analysis, electrophoresis, and any combination thereof.

The present invention further comprises a kit or kits to carry out the methods of this invention. A kit of this invention can comprise reagents, buffers, and apparatus for mixing, measuring, sorting, labeling, etc, as well as instructions and the like as would be appropriate for genotyping the 33 SNPs of Table 1 in a nucleic acid sample. The kit may further comprise control reagents, e.g., to identify markers for a specific ethnicity or gender.

The present invention is more particularly described in the following examples that are intended as illustrative only since numerous modifications and variations therein will be apparent to those skilled in the art.

EXAMPLES

Example 1. Patient A

A 40 year old Caucasian man with a significant family history of prostate cancer with his father and paternal grandfather dying of the disease, sees his primary care physician, asking him about PCa risk and if and/or when to begin prostate cancer screening. He is referred to his urologist who counsels him about the risks and benefits of prostate cancer screening and offers him a genetic test based on 33 SNPs which can measure his baseline risk for PCa. He accepts and has a sample of his nucleic acid tested.

He sees his urologist who goes over the report of the genetic test, which describes the patient's risk for PCa based only on his genetic profile in several formats:

CRR: 2.40
Percentile risk: $96^{th}$ percentile
Absolute risk: 0.31
PCa risk score: 0.37

Given the above report, the patient comes to the conclusion that he is at high risk for PCa and decides to pursue PSA-based PCa screening. This is based on the fact that he is at 2.4 fold increase in risk for PCa as compared to the general population and that only 4% of the population has a higher risk for prostate cancer. Furthermore, for him, a lifetime, absolute risk of 31% is high and warrants follow-up. To date, there is no well established clinical parameter applicable to the 40 year old male with the exception of possibly family history. We have already demonstrated (Table 2) that the genetic test outperforms family history, the only other potentially applicable existing clinical predictor of PCa risk. In addition, family history may not be available in some cases such as adoption, lack of male family members and a lack of communication between family members.

Example 2. Patient B

Patient A's 50 year old brother heard from his brother about the above-described genetic test for PCa risk. He had his first ever PSA, which was borderline high at 4.0 ng/ml. He has heard that prostate biopsy is very uncomfortable and would like to avoid it if at all possible. Based on his initial clinical parameters, his urologist offers him a prostate biopsy. He undergoes the genetic testing, which gives him the following result:

CRR: 0.90
Percentile risk: $49^{th}$ percentile
Absolute risk: 0.12
PCa risk score: 0.19

On the basis of this report, he concludes that he is at lower risk for PCa and opts to continue to follow his PSA as opposed to proceeding directly to prostate biopsy. He makes this decision based on the subjective judgment that, for him, an absolute risk of 12% is low. In addition, he knows that based on a CRR of 0.9 and a percentile risk of $49^{th}$ percentile, that the majority of the population is at higher risk than him. He has confidence in a stable result such as the genetic profile as compared to PSA, which can fluctuate due to other, benign causes. Furthermore, the PSA cut-point of 4.0 ng/ml is a borderline result; addition of genetic information provided further guidance to allow for a meaningful decision.

Example 3. Patient C

Patient A&B's 60 year old brother heard from his brother about the above-described genetic test for PCa risk. He has been seeing a urologist for five years regarding an elevation in his PSA and he had a negative biopsy two years ago. His PSA is continuing to climb and he and his urologist are considering a repeat biopsy. He sees his urologist to consider what additional information this new genetic test may offer. Together he and his urologist decide that he will have this genetic test done. His nucleic acid sample, along with his clinical information (age, family history, PSA, F/T PSA ratio, prostate volume from his last biopsy and number of negative cores at the time of his biopsy) are sent in for analysis. He returns to his urologist's office for the results of his tests, which are as follows.

CRR: 2.52
Percentile risk: 95th percentile
Absolute risk: 0.32
PCa risk score: 0.37

Given the above profile information, Patient C decides to undergo a repeat prostate biopsy, which is positive for Gleason 3+4 PCa. He undergoes a radical prostatectomy and is cured. Provision of his genetic risk allowed for the patient to be able to have an outside objective assessment of his risk, which is apart from the currently available predictors which were abnormal and prompted the initial biopsy. For patient C, with a 2.5 fold higher risk with only 5% of the population at higher risk and an absolute risk of 32%, in his opinion, especially given his family history, he wished to pursue repeat biopsy.

Example 4. Methods of Genetic Test to Determine Genetic Score

In a hierarchical order, three models were used to predict PCa risk. First, we used a "genetic marker only" model in which 33 SNPs identified by genome wide association studies (GWAS) as associated with PCa risk were included. Second, we used a "genetic marker+pre-biopsy variable model"; in addition to the 33 SNPs, this model included age, family history, and ratio of baseline free PSA to baseline total PSA. Third, we used a "genetic+pre-biopsy variable+ post-biopsy variable model"; in addition to the second model, this model included baseline prostate volume and number of previous biopsy cores. We used each model to perform risk assessment, which included estimating various measures of PCa risk, including the cumulative relative risk (CRR), percentile risk, absolute risk, and risk score (i.e., the predicted probability of being diagnosed with PCa as determined by a regression model). The predictive performance of each model is measured by detection rate of PCa during the four years of the REDUCE trial, providing an overall assessment of clinical validity. Detailed methods for estimating these measures of risk are described below.

Odds Ratio (OR) Calculations.

ORs for the 33 SNPs were calculated using external data presented in the literature. ORs for the clinical variables were estimated from the study sample. For the allelic ORs, we obtained the best estimates and their confidence intervals (CIs) for the 33 SNPs using meta-analysis. The details of the meta-analysis are described below. First, if the literature search yielded raw data such as allele counts of case and control, then we used this information for calculating the OR and standard error for each study population. Otherwise, we calculated these estimates using the reported OR and 95% CI. The results from both approaches are statistically comparable. Second, while integrating different study results, we began by assessing the heterogeneity of estimated ORs across study populations. The Q-statistic (for test of heterogeneity) and I2 statistic (which measures the proportion of total variance in estimated ORs due to heterogeneity) were used. If there was evidence of a high degree of heterogeneity, such as a value of the I2 statistic greater than 50%, then the random effects method was used to calculate the pooled OR and CI. Otherwise, the fixed effects method was used. The fixed effects method weighs each study with the inverse of variance of logarithm of OR, while the random effects method additionally incorporates variance in that weight. Furthermore, the ORs for the demographic and clinical variables were calculated by applying the multiple logistic regression in our own study sample since they were not available from the meta-analysis. Each of the demographic or clinical variables has been categorized with meaningful cut-off points.

Relative Risk (RR) Calculation.

For each of the three genotypes at each SNP, the allelic OR was converted to the RR relative to the general population using the following approach. The average population risk compared to non-carriers was a weighted average of the relative risks of the genotypes. Specifically, the ratio between the average population risk and the risk of non-carriers was estimated by $A=P(rr) \times OR^2+P(wr) \times OR+P(ww)$, where w is the wild type allele, r is the risk allele, and P(ww), P(wr), and P(rr) are the proportions of the population carrying ww, wr, and rr, respectively. RRs for ww, wr, and rr were estimated by 1/A, OR/A, and $OR^2/A$, respectively. The corresponding confidence intervals were estimated accounting for variability of estimates of OR. Furthermore, the RRs for the clinical variables were calculated in the similar manner. The ratio between the average population risk and the risk of the reference group was estimated by summing over the product of frequency of each category and the corresponding OR. Then the RR was calculated accordingly.

Measures of Risk.

Cumulative relative risk (CRR), percentile risk to PCa, absolute risk, and risk score were used as measures of risk to PCa in this study. To estimate cumulative relative risk, we assumed the controls were a random sample from the general population. For the genetic only model, a multiplicative model was used, in which we multiplied the RRs for each of the SNPs for a given individual. For the other two models, the CRR relative to the population was derived by combining the RRs for the 33 SNPs as well as RRs for the clinical variables of the individual by simple multiplication. The percentile risk to PCa was generated by determining the risk level in terms of percentile within the distribution of population CRR.

The absolute risk for each individual was then estimated based on the overall CRR, relative to the population (r(a,x)), the incidence rate of PCa in the general population ($\lambda_0(x)$), and the all-cause mortality rate excluding PCa in the United States ($\mu_0(x)$). Specifically, assuming the mortality data are known without error and do not vary with the risk factors in our model, we used mortality data from the National Center of Health Statistics to estimate the mortality rate from non-PCa causes. Let F(a,t) denote the probability that one survives until age t without developing PCa. Then F(a,t)= $\exp\{-\int_a^t [r(a,x)\lambda_0(x)+\mu_0(x)]dx\}$. The probability that one develops PCa in a small interval equals the probability of his/her disease free survival until age t times the conditional probability of developing PCa by age t+Δt given that one was disease free at age t. This probability, absolute risk, is conditioned on the fact that one has not developed PCa by age a. The corresponding CIs can be calculated accounting for the variability of estimates of relative risks and of risk factor distributions.

The risk score was the predicted value of PCa risk from a logistic regression model with the CRR from the genetic component alone or in combination with other clinical variables as the covariate. It is calculated as $$\frac{\exp(\hat{\beta}_0 + \hat{\beta}_1 X)}{1 + \exp(\hat{\beta}_0 + \hat{\beta}_1 X)},$$

where X is the relative risk, $\hat{\beta}_0$ and $\hat{\beta}_1$ are regression coefficient estimates for the intercept and relative risk, respectively. The corresponding CI can be calculated by converting the CIs for the linear combination of the estimated coefficients and the values of the relative risk (i.e., $\hat{\beta}_0+\hat{\beta}_1 X$).

Figure 6:
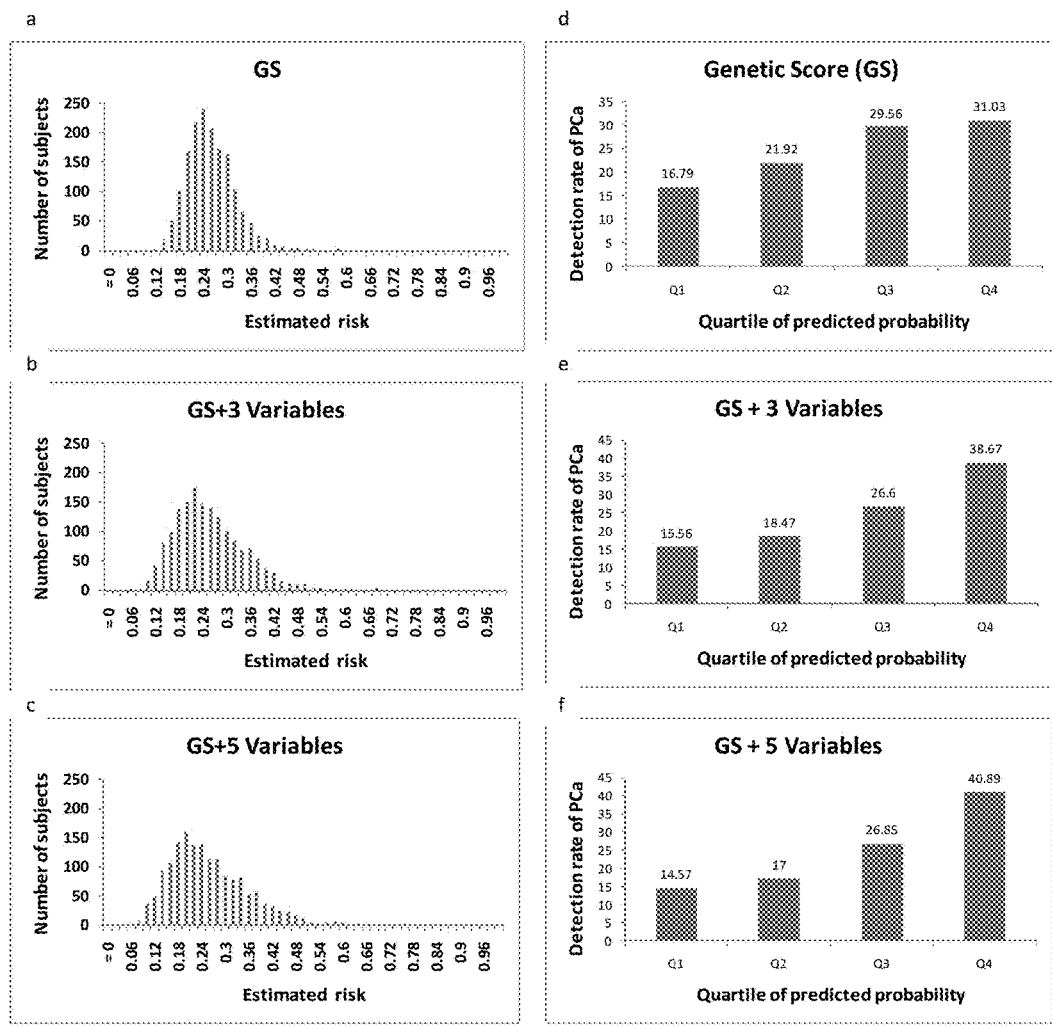
FIG. 6, panels a-f.

The distributions of risk score among the REDUCE study subjects are presented in FIG. 6, panels a-c for genetic marker only, genetic marker+pre-biopsy variable model," and "genetic+pre-biopsy variable+post-biopsy variable model," respectively.

Detection Rate.

In order to assess clinical validity, the detection rate of PCa during the 4-year study of the REDUCE study was calculated for each model to measure their predictive performance. We divided the sample equally into quartiles based on the estimated risk of risk. Detection rate was then calculated as the proportion of positive biopsies in each quartile. To obtain unbiased estimates, four-fold cross-validation was used to calculate detection rates. Four-fold cross validation randomly divides the data into four (roughly) equal subsets and repeatedly uses three subsets for model fitting (training) and the remaining subset for validation (testing), in order to calculate the detection rate. This process was repeated until each of the four subsets had been used exactly once as validation data, after which detection rates were averaged across results from each of the 4 validation sets. All of the detection rates in the testing samples of four-fold cross validation were reported except for the genetic model, because the genetic score was calculated based on external OR estimates of the 33 SNPs. The observed detection rates of PCa during the four-year REDUCE study are presented in FIG. 6, panels d-f for men at each quartile of estimated risk based on genetic marker only, genetic marker+pre-biopsy variable model," and "genetic+pre-biopsy variable+post-biopsy variable model," respectively.

In some embodiments of this invention, a genetic score that places an individual in the 50th percentile or greater is indicative of increased risk of PCa. An absolute risk value of greater than about 0.13 is indicative of increased risk of PCa. A CRR of greater than 1.0 is indicative of increased risk of PCa. A genetic score that places an individual below the 50th percentile is indicative of decreased risk of PCa. An absolute risk value of less than about 0.13 is indicative of decreased risk of PCa. A CRR of less than 1.0 is indicative of decreased risk of PCa. Increased risk and decreased risk as used herein mean increased or decreased relative to the general population (see, e.g., SEER information at http://seer.cancer.gov).

Furthermore, a population median risk score can be used as the cutoff for indicating increased or decreased risk (i.e., a risk score above the cutoff indicates increased risk and a risk score below the cutoff indicates decreased risk). This differs for each of the three models. For genetic only model, the cutoff is 0.24, for genetic+pre-biopsy model, the cutoff is 0.23 and for genetic+pre-biopsy+post-biopsy, the cutoff is 0.23.

Increased risk and decreased risk as used herein mean increased or decreased relative to the general population.

Example 5. Clinical Utility of Inherited Markers in Determining Need for Repeat Biopsy: Results from Placebo Arm of the Reduce® Study (Abstract)

Purpose.

Management of men following negative prostate biopsy for prostate cancer is challenging. The predictive performance of currently available clinical parameters such as prostate specific antigen (PSA) for prostate cancer is limited. Recently, 33 PCa risk-associated single nucleotide polymorphisms (SNPs) have been identified from genome-wide association studies. The present study provides an assessment of supplementing existing predictors with the prediction of prostate cancer on subsequent biopsy.

Methods.

Study subjects included 1,654 men in the placebo arm of the four-year randomized REduction by DUtasteride of prostate Cancer Events (REDUCE®) trial, where all subjects had PSAs between 2.5-10.0 ng/mL, a negative prostate biopsy at baseline and underwent scheduled prostate biopsies at years 2 and 4.

Results.

Of 1,654 men who had at least one prostate biopsy over four years, 410 (25%) and 124 (7%) were diagnosed with prostate cancer and high-grade PCa (Gleason grade≥7), respectively. Differences in the genetic score between men with positive and negative biopsies were highly significant even after adjusting for other clinical variables ($P=3.58\times10^{-8}$). The AUC for prostate cancer prediction of the genetic score was 0.59, higher than any other individual clinical parameters including PSA (AUC=0.54). When the genetic score was added to the best clinical model including five parameters (age, family history, free/total PSA ratio, prostate volume, and number of cores at base biopsy), the AUC increased from 0.60 to 0.64. The differences in detection rates between men with lower or higher genetic risk at each quartile of estimated risk based on the best clinical model ranged from 9.31% to 13.66% for prostate cancer and 2.89 to 6.16% for high-grade prostate cancer, providing strong evidence for the added value of genetic markers in risk prediction.

Conclusions.

For men with an initial negative biopsy, genetic markers may be used to supplement existing predictors to better predict for prostate cancer and high-grade prostate cancer on subsequent biopsy.

Example 6. Clinical Utility of Inherited Genetic Markers for the Prediction of Prostate Cancer at Repeat Biopsy: Results from Placebo Arm of the Reduce Clinical Trial (Manuscript)

Background.

The predictive performance of available clinical parameters for prostate cancer (PCa) is limited, particularly following negative prostate biopsy. We sought to assess the clinical utility of identified PCa risk-associated single nucleotide polymorphisms (SNPs) for PCa prediction in a clinical trial.

Methods.

Subjects included 1,654 men who consented for genetic studies in the placebo arm of the randomized REduction by DUtasteride of Prostate Cancer Events (REDUCE) trial, where all subjects had a negative prostate biopsy at baseline and underwent scheduled prostate biopsies at years 2 and 4. Predictive performance of clinical parameters at baseline, and/or a genetic score based on 33 PCa risk-associated SNPs was evaluated using the area under the receiver operating characteristic curve (AUC) and PCa detection rate.

Findings.

Of the 1,654 men, 410 (25%) were diagnosed with PCa during the four year follow-up. The genetic score based on the 33 SNPs was a highly significant predictor for positive biopsy even after adjusting for known clinical variables (P=3.58×10$^{-8}$). Measured by AUC, the genetic score outperformed any individual clinical parameter including prostate-specific antigen (PSA) for PCa risk prediction, and improved the performance of the best combined clinical model consisting of age, family history, free/total PSA ratio, prostate volume, and number of initial biopsy cores. The added value of the genetic score is highlighted by its ability to further differentiate PCa detection rates defined by the best clinical model. The observed PCa detection rate over 4-years was 19.16% higher for men with higher estimated clinical risk/higher genetic score (34.82%) than with lower estimated clinical risk/lower genetic score (15.66%), P=3.3×10$^{-10}$.

Interpretations.

This clinical trial provides the next level of evidence, that germline markers may be used to supplement existing clinical parameters to better predict outcome of prostate biopsy.

Introduction.

Prostate cancer (PCa) is the most common solid organ malignancy affecting American men and the second leading cause of cancer related death.[1] Approximately one million prostate biopsies are performed yearly in the U.S. The vast majority of these biopsies are performed due to elevated levels of the PCa marker prostate-specific antigen (PSA). However, only a quarter of these biopsies result in a diagnosis of PCa, highlighting the inadequate performance of PSA to predict PCa. Persistently elevated PSA levels and/or other clinical parameters that prompted initial biopsies contribute to stress and anxiety among both patients and their urologists.[2] Novel biomarkers are urgently needed to better determine the need for initial and repeat prostate biopsy.

Recently, more than 30 PCa risk-associated single nucleotide polymorphisms (SNPs) have been discovered from genome-wide association studies (GWAS).[3-13] These risk-associated SNPs have been consistently replicated in multiple case-control study populations of European descent.[14] Although each of these SNPs is only moderately associated with PCa risk, a genetic score based on a combination of risk-associated SNPs can be used to identify men at high risk for PCa.[15-18] These risk-associated SNPs may have broad practical applications because they are common in the general population.

Study Population.

Subjects included 1,654 of the 3,129 (53%) men of European descent in the placebo arm of the randomized, multi-institutional, international, Reduction by DUtasteride of Prostate Cancer Events (REDUCE) study who consented for genetic studies. The characteristics of patients who consented or declined genetic studies are presented in Table 3. The REDUCE study is a randomized double blind chemoprevention trial, examining PCa risk reduction by dutasteride, a dual 5-alpha reductase inhibitor, in a population of men with prior negative prostate biopsy.[19] Eligible men were 50 to 75 years of age, with a serum PSA≥2.5 ng/mL and ≤10 ng/mL (men aged 50-60 years) or ≥3.0 ng/mL and ≤10 ng/mL (men>60 years of age), and had a single, negative prostate biopsy (6-12 cores) within 6 months prior to enrollment (independent of the study). Exclusion criteria included more than one prior prostate biopsy, high-grade prostatic intra-epithelial neoplasia (HG-PIN) or atypical small acinar proliferation (ASAP) on the pre-study entry prostate biopsy assessed by a central pathology laboratory, or a prostate volume greater than 80 cc.

PCa Risk-Associated SNPs, Ancestry Informative Markers (AIMs), and Genotyping.

A panel of 33 PCa risk-associated SNPs were selected from all PCa GWAS reported before December 2009 (Table 4). Each of these SNPs exceeded genome-wide significance levels in their initial reports (P<10$^{-7}$) and these associations have been replicated in independent study populations.[3-13] In addition, 91 SNPs from a panel of 93 AIMs were genotyped to distinguish population groups from major continents.[20] These SNPs were genotyped using the Sequenom MassARRAY platform. One duplicated CEPH (Centre d'Etude du Polymorphisme Humain) sample and two water samples (negative controls) that were blinded to technicians were included in each 96-well plate. The concordance rate between the two genotype calls of the duplicated CEPH sample for all SNPs was 100%.

Statistical Analyses.

Allelic odds ratios (ORs) and 95% confidence intervals (CIs) for each of the 33 SNPs were estimated using an unconditional logistic regression model, adjusting for ethnic structure using the first two principal components, as is standard in genetic association studies.[20-21] (Table 4). A genetic score, based on all 33 SNPs and OR estimates from an external meta-analysis, was calculated for each individual.[22] Briefly, a multiplicative model was used to derive genotype relative risks from the external allelic OR. For each of the three genotypes at each SNP, the genotype relative risk was converted to the risk, relative to the population. The overall risk, relative to the population (i.e., genetic score), was derived by combining the risks, relative to the population, of all SNPs of each individual by simple multiplication.

Chi-square and t-tests were used to compare the differences between groups of subjects for binary variables (family history, digital rectal exam [DRE], and continuous variables (age, PSA measurements, prostate volume, number of cores at pre-study entry biopsy, and genetic score), respectively. Total PSA and genetic score were log transformed to approach a normal distribution.

The AUC of clinical predictors and genetic score, individually and in combination, for predicting PCa was estimated using a logistic regression model. Four-fold cross validation was used to reduce the bias in estimates of AUC. Subjects were randomly divided into four groups. A model was fit to each three-quarter subset of the subjects and tested on the remaining one-quarter subset of subjects, yielding four testing AUCs. Results from 10 runs of four-fold cross validation are reported.

We also calculated the detection rate of PCa for men at various estimated risk categories based on prediction models. Unbiased detection rates were directly estimated for the genetic model, because the genetic score of each individual was calculated based on external OR estimates of the 33 SNPs. For the clinical model, four-fold cross validation was used to obtain unbiased estimates, as described below. Coefficients of variables in the prediction models were estimated from each three-quarter subset of the subjects and used to calculate risk in the remaining one-quarter subset of subjects. Each of these one-quarter subsets of subjects was ranked based on estimated risk and then equally divided into two groups. The PCa detection rate was calculated as the proportion of positive biopsy in each group. Results from 10 runs of four-fold cross validation are reported.

Results.

Among the 1,654 men of European descent who had an initial negative biopsy for PCa and who consented to genetic studies in the placebo arm of the REDUCE trial, 410 men (25%) had a positive prostate biopsy for PCa from scheduled and for-cause biopsies over the four-year study. In a univariate analysis (Table 1), men with positive biopsies differed significantly (P<0.05) from men with negative prostate biopsies for all of the baseline clinical and demographic variables, with the exception of DRE. Significant differences were also observed for genetic risk factors; positive family history of PCa was found in 17% of the men with positive biopsy, compared with 12% of the men with negative biopsy (OR=1.5 [95% CI: 1.09-2.04], P=0.01), and the difference in the genetic score between these two groups was highly significant (P=4.95×10$^{-9}$). After adjusting for known PCa risk-associated clinical variables such as age, free/total PSA ratio, number of cores at initial biopsy, and prostate volume using multivariate logistic regression analysis, family history and genetic score remained significantly associated with positive prostate biopsy (P=0.002 and 3.58×10$^{-8}$, respectively).

We calculated the AUC of these baseline clinical variables and genetic risk factors, individually and in combination, for predicting positive prostate biopsy during the four-year follow-up. To obtain unbiased estimates of AUC, a four-fold cross validation method was used and results from testing samples are reported (Table 2). Among individual predictors, the AUC of the genetic score was highest (0.59), followed by prostate volume (0.56), age (0.56), number of cores sampled at pre-study entry biopsy (0.55), free/total PSA ratio (0.54), total PSA (0.54), family history (0.52), and DRE (0.51). When multiple predictors were included in the model simultaneously, the best clinical model included five baseline variables (age, family history, free/total PSA ratio, number of cores at pre-study entry biopsy, and prostate volume), with an AUC of 0.60. When the genetic score was added to this best clinical model, the AUC increased to 0.64.

To facilitate the use and interpretation of these models in predicting positive prostate biopsy, we calculated the PCa detection rate during four years for the genetic score model and the best clinical model. Each individual's risk for PCa was estimated using either the genetic score model or the best clinical model, and was classified as being lower or higher risk for PCa (compared to the median risk) under each model. The observed detection rates of PCa for men at different estimated risks under each model are presented in FIG. 1, panels a-b. Both the genetic model and the best clinical model were able to differentiate detection rate between these two groups of men, although the genetic model performed better. In the genetic model, the observed detection rate was 11.60% higher for men who had higher estimated risk (30.59%) than those with lower estimated risk (18.99%). The difference was highly significant, P=4.6×10$^{-8}$. In the best clinical model, the observed detection rate was 8.65% higher for men who had higher estimated risk (29.16%) than those with lower estimated risk (20.51%). The difference was also significant, P=5.4×10$^{-5}$.

Figure 2:
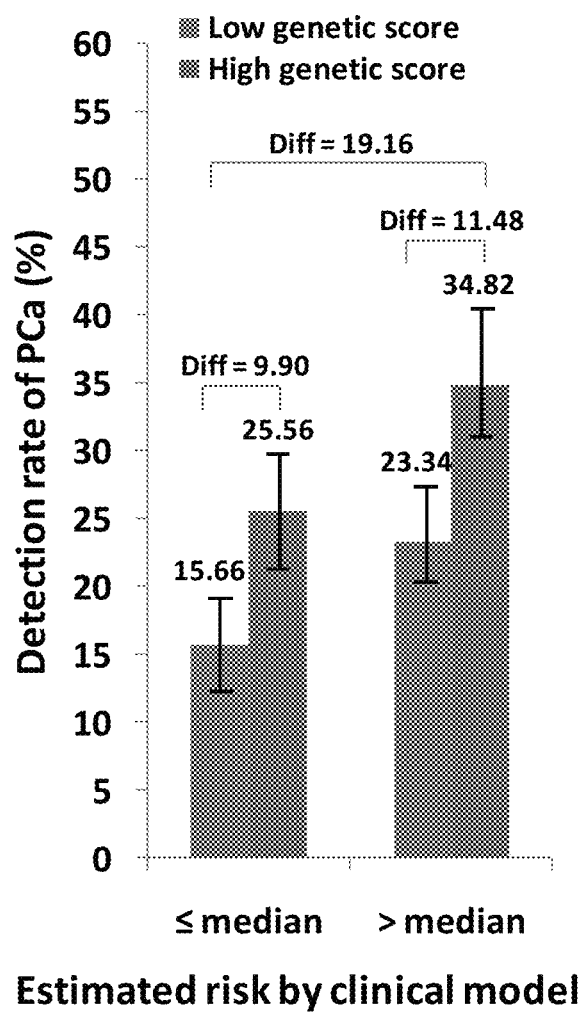
FIG. 2. Detection rates for prostate cancer for men below or above the median estimated risk based on the best clinical model (age, family history, free/total PSA ratio, prostate volume, and number of cores at initial biopsy), and stratified by genetic risk (lower or higher half of genetic risk). Vertical lines in each bar represent 95% CI of detection rates.

To further examine the value of adding the genetic score to existing clinical parameters in predicting positive prostate biopsy, we estimated PCa detection rates among men who were classified as the same risk based on the best clinical model but having different genetic scores (FIG. 2). The genetic score was able to further differentiate detection rate. For men at lower clinical risk, the detection rate for PCa was 9.90% higher for men whose genetic score was above the median (25.56%) than those below the median (15.66%), P=4.9×10$^{-4}$. Similarly, for men at higher clinical risk, the detection rate for PCa was 11.48% higher for men who had higher genetic score (34.82%) than lower genetic score (23.34%), P=3.2×10$^{-4}$. Combining the genetic model and the best clinical model, they were able to considerably differentiate detection rate between the extreme groups of men. The detection rate was 19.16% higher for men who have higher estimated clinical risk/higher genetic score (34.82%) than men who had lower estimated clinical risk/lower genetic score (15.66%), P=3.3×10$^{-10}$.

Figure 3:
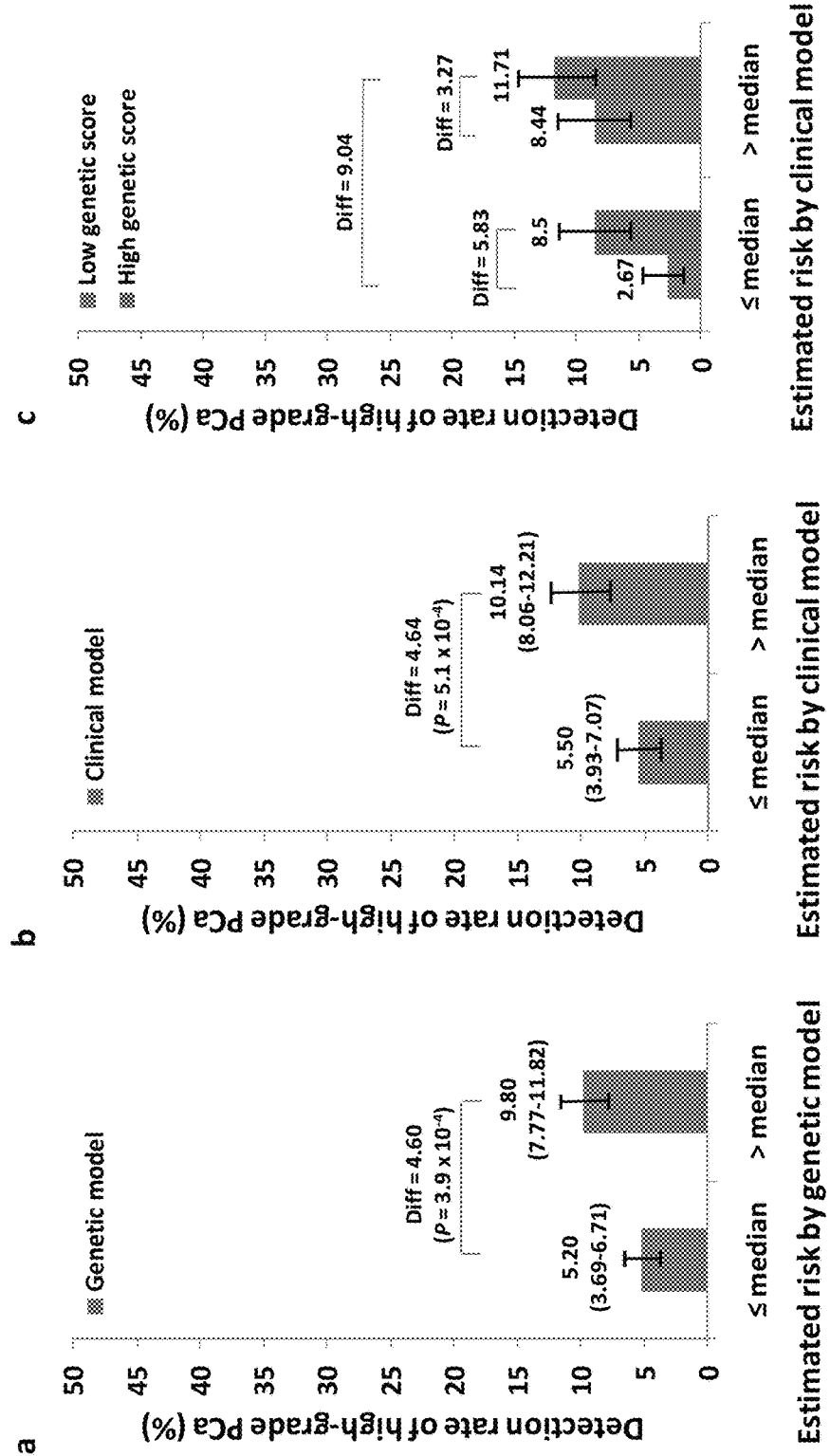
FIG. 3. Detection rates for high-grade prostate cancer for men below or above the median estimated risk based on panel a) the genetic model, panel b) the best clinical model (age, family history, free/total PSA ratio, prostate volume, and number of cores at initial biopsy), and panel c) the best clinical model and stratified by genetic risk (lower or higher half of genetic risk). Vertical lines in each bar represent 95% CI of detection rates.

To preliminarily evaluate the performance of genetic score and clinical parameters in distinguishing risk for high-grade PCa, we compared the detection rate of high-grade PCa among men with various estimated risk under these two models. Among the 410 men who were diagnosed with PCa, 124 (30%) had high-grade PCa (Gleason grade≥7). Higher detection rates were observed among men with higher estimated risk compared to those with lower risk under the genetic model (FIG. 3, panel a), the best clinical model (FIG. 3, panel b), and the combination of both models (FIG. 3, panel c).

Results from several retrospective case-control studies have suggested that PCa risk-associated SNPs discovered from GWAS may be used to predict an individual's risk for PCa, providing the possibility that they may be used for targeted screening and chemo-prevention of PCa.[15-16] However, due to limitations of the case-control study design, a number of key questions have remained prior to their clinical use. The first fundamental question is whether these SNPs are associated with elevated PSA and not PCa risk per se, as elevated PSA leads to more prostate biopsies and in turn a greater PCa detection rate as is seen in case control studies (i.e., PSA detection bias).[23] Another important question is the assessment of predictive performance of genetic markers and clinical variables such as PSA in the same study, and more importantly whether genetic markers significantly improve the ability of existing clinical parameters to predict PCa. These questions are difficult to address in case-control studies as these clinical variables are commonly used as part of PCa screening.

The placebo arm of the REDUCE study, a large randomized clinical trial, provides a unique opportunity to answer these two important questions. All men in the study had a negative biopsy at baseline and were followed-up for four years, with scheduled not-for-cause (i.e., regardless of PSA levels and other clinical indications) prostate biopsies at years 2 and 4. Therefore, this study design minimizes the potential impact of PSA detection bias on associations between PCa risk and SNPs. In addition, because it is a clinical trial, a number of clinical variables, such as free/total PSA ratio and prostate volume were measured at baseline using a standardized protocol. To our knowledge, this is the first reported study to validate these PCa risk-associated SNPs and assess their value when added to existing clinical variables for the prediction of PCa risk in a large prospective clinical trial.

In this study, we found that the genetic score is a significant predictor of positive prostate biopsy and that this association is independent of known clinical parameters and family history (P=3.58×10$^{-8}$). Considering that the genetic score was based on all 33 a priori established PCa risk-associated SNPs and using OR estimates obtained from external study populations, these results provide the highest level of independent evidence of the validity of these genetic markers to predict an individual's risk for PCa. In addition, through a direct comparison of the predictive performance (AUC) of genetic markers and existing clinical variables in the same study population, we showed that the genetic score outperformed any other individual clinical parameter, including PSA, for PCa risk prediction. More importantly, the genetic score improved the AUC when added to a model including the best, existing clinical variables.

The strongest support for the predictive performance of genetic markers and added value of genetic markers to the existing clinical variables in this population is demonstrated by the measurement of detection rate of PCa. The ~10% difference in detection rate of PCa between higher or lower genetic score and ~20% difference between the two extreme groups (men with lower clinical risk and lower genetic score, or higher clinical risk and higher genetic score) may be clinically significant. This improvement is worth noting considering that few other biomarkers in the past several decades, be they proteins or genetic markers, have reached such a level. It is also important to note that detection rate, as a measurement of predictive performance, can be easily understood and interpreted by physicians and patients. This is in contrast to AUC, another commonly used measurement of predictive performance, where the value is not directly related to meaningful clinical measurements.

There are fundamental differences between the genetic score and clinical variables. An advantage of clinical variables is that they directly assess parameters that are associated with the development of the disease. On the other hand, the genetic score assesses the likelihood of developing disease and thus is time-independent. It can be assessed at any stage, before or after the development of disease. The high stability of DNA molecules as well as accurate and low cost genotyping of genetic markers also facilitates their clinical implementation. Some potential applications of genetic markers may include the identification of high risk men at a younger age for PCa screening and chemoprevention, as well as supplementation of the clinical variables to determine the need for biopsy or, as in this study, the need for repeat biopsy.

Results from this study not only add further support for the utility of genetic markers in predicting PCa risk but also provide new information that is urgently needed for the management of the ~750,000 American men yearly who have a negative prostate biopsy. Currently, PSA levels and free/total PSA ratio are the primary predictors used to determine the need and interval for repeat prostate biopsy.[2] Their ability to predict PCa is unsatisfactory, with published AUCs in the 0.60-0.75 range.[24-26] The predictive performance of PSA was even lower in our study, with an AUC of 0.54 for total PSA or free/total PSA ratio. The lower AUC estimate in our study may be due to the repeat biopsy population or the fewer PSA-driven biopsies (less than 7% PCa were detected by protocol-independent biopsies).[19] In addition, the AUCs reported in our study were based on testing samples of four-fold cross-validation, which minimizes the upward bias due to model over-fitting. Regardless of the different estimates of AUC from different studies, the generally low AUC in all of the studies points to the need for additional markers to better guide indications for repeat biopsy and determine the timing of follow-up. To this end, this study has successfully demonstrated that a genetic score based on PCa risk-associated SNPs may be one of these much needed markers.

There are several notable limitations in this study. One of the most important drawbacks was that the study was limited to subjects of European descent. This is in part due to the fact that PCa risk-associated SNPs were discovered in men of European descent. The relevance of these SNPs in other races is unknown, although PCa associations with several of these risk-associated SNPs have been confirmed in men of African American, Asian, and Hispanic race.[27] Furthermore, only a small number of men of non-European descent participated in the REDUCE trial,[19] thus significantly limiting the power to draw any conclusions beyond this one ethnicity. Another important limitation was that we did not directly assess the ability of these genetic markers to independently discriminate risk between high-grade and low-grade PCa, although we have demonstrated the added value of the genetic score for predicting high-grade PCa by detection rate. Several studies have previously suggested that these 33 SNPs are not able to distinguish risk for aggressive PCa from its more indolent form.[28-29] In addition, due to the relatively low frequency of high-grade PCa patients in this study, the statistical power is limited. Finally, it is important to note that the predictive performance of the best clinical model and genetic model remain poor.

Our study validated the association of a genetic score based on 33 SNPs with PCa risk in the context of a prospective clinical trial, and for the first time, demonstrated the added value of genetic markers to the existing clinical variables for PCa prediction. The improvement of genetic markers in predicting PCa, albeit moderate, is much needed for urologists and their patients to determine the need for biopsy, and in particular repeat biopsy, for PCa detection.

REFERENCES FOR EXAMPLE 6

1. Jemal A, Siegel R, Ward E, Hao Y, Xu J, Thun M J. Cancer statistics, 2009. *CA Cancer J Clin.* 2009; 59:225-249.
2. Presti J C Jr. Repeat prostate biopsy—when, where, and how. *Urol Oncol.* 2009; 27:312-314.
3. Amundadottir L T, Sulem P, Gudmundsson J, Helgason A, Baker A, Agnarsson B A, et al. A common variant associated with prostate cancer in European and African populations. *Nat Genet.* 2006; 38:652-658.
4. Gudmundsson J, Sulem P, Manolescu A, Amundadottir L T, Gudbjartsson D, Helgason A, et al. Genome-wide association study identifies a second prostate cancer susceptibility variant at 8q24. *Nat Genet.* 2007; 39:631-637.
5. Yeager M, Orr N, Hayes R B, Jacobs K B, Kraft P, Wacholder S et al. Genome-wide association study of prostate cancer identifies a second risk locus at 8q24. *Nat Genet.* 2007; 39:645-649.
6. Gudmundsson J, Sulem P, Steinthorsdottir V, Bergthorsson J T, Thorleifsson G, Manolescu A, et al. Two variants on chromosome 17 confer prostate cancer risk, and the one in TCF2 protects against type 2 diabetes. *Nat Genet.* 2007; 39:977-983.
7. Duggan D, Zheng S L, Knowlton M, Benitez D, Dimitrov L, Wiklund F, et al. Two genome-wide association studies of aggressive prostate cancer implicate putative prostate tumor suppressor gene DAB2IP. *J Natl Cancer Inst.* 2007; 99:1836-1844.
8. Thomas G, Jacobs K B, Yeager M, Kraft P, Wacholder S, Orr N et al. Multiple loci identified in a genome-wide association study of prostate cancer. *Nat Genet.* 2008; 40:310-315.
9. Gudmundsson J, Sulem P, Rafnar T, Bergthorsson J T, Manolescu A, Gudbjartsson D, et al. Common sequence variants on 2p15 and Xp11.22 confer susceptibility to prostate cancer. *Nat Genet.* 2008; 40:281-283.
10. Eeles R A, Kote-Jarai Z, Giles G G, Olama A A, Guy M, Jugurnauth S K, et al. Multiple newly identified loci associated with prostate cancer susceptibility. *Nat Genet.* 2008; 40:316-321.
11. Yeager M, Chatterjee N, Ciampa J, Jacobs K B, Gonzalez-Bosquet J, Hayes R B, et al. Identification of a new prostate cancer susceptibility locus on chromosome 8q24. *Nat Genet.* 2009; 41:1055-1057.

12. Gudmundsson J, Sulem P, Gudbjartsson D F, Blondal T, Gylfason A, Agnarsson B A, et al. Genome-wide association and replication studies identify four variants associated with prostate cancer susceptibility. *Nat Genet.* 2009; 41:1122-1126.
13. Eeles R A, Kote-Jarai Z, Al Olama A A, Giles G G, Guy M, Severi G, et al. Identification of seven new prostate cancer susceptibility loci through a genome-wide association study. *Nat Genet.* 2009; 41:1116-1121.
14. Easton D F, Eeles R A. Genome-wide association studies in cancer. *Hum Mol Genet.* 2008; 15; 17(R2):R109-R115.
15. Zheng S L, Sun J, Wiklund F, Smith S, Stattin P, Li G, et al. Cumulative association of five genetic variants with prostate cancer. *N Engl J Med.* 2008; 358:910-919.
16. Xu J, Sun J, Kader A K, Lindström S, Wiklund F, Hsu F C, et al. Estimation of absolute risk for prostate cancer using genetic markers and family history. *Prostate.* 2009; 69(14): 1565-1572.
17. Salinas C A, Koopmeiners J S, Kwon E M, FitzGerald L, Lin D W, Ostrander E A, et al. Clinical utility of five genetic variants for predicting prostate cancer risk and mortality. *Prostate.* 2009; 69(4):363-372.
18. Fitzgerald L M, Kwon E M, Koopmeiners J S, Salinas C A, Stanford J L, Ostrander E A. Analysis of recently identified prostate cancer susceptibility loci in a population-based study: associations with family history and clinical features. *Clin Cancer Res.* 2009; 15:3231-3237.
19. Andriole G A, Bostwick D, Brawley O W. The influence of dutasteride on the risk of biopsy-detectable prostate cancer: Outcomes of the REduction by DUtasteride of Prostate Cancer Events (REDUCE) study. *N Engl J Med.* 2010; 362(13): 1192-1202.
20. Nassir R, Kosoy R, Tian C, White P A, Butler L M, Silva G, et al. An ancestry informative marker set for determining continental origin: validation and extension using human genome diversity panels. *BMC Genet.* 2009; 10:39.
21. Price A L, Patterson N J, Plenge R M, Weinblatt M E, Shadick N A, Reich D, et al. Principal components analysis corrects for stratification in genome-wide association studies. *Nat Genet.* 2006; 38:904-909.
22. Kim S-T, Cheng Y, Hsu F-C, Jin T, Kader A K, Zheng S L, et al. Prostate cancer risk-associated variants reported from genome-wide association studies: meta-analysis and their contribution to genetic variation. *Prostate.* 2010 Jun. 16
23. Ahn J, Berndt S I, Wacholder S, Kraft P, Kibel A S, Yeager M, et al. Variation in KLK genes, prostate-specific antigen and risk of prostate cancer. *Nat Genet.* 2008; 40:1032-1034.
24. Djavan B, Zlotta A, Remzi M, Ghawidel K, Basharkhah A, Schulman C C, et al. Optimal predictors of prostate cancer on repeat prostate biopsy: a prospective study of 1,051 men. *J Urol.* 2000; 163(4):1144-1148.
25. Yanke B V, Gonen M, Scardino P T, Kattan M W. Validation of a nomogram for predicting positive repeat biopsy for prostate cancer. *J Urol.* 2005; 173(2):421-424.
26. Thompson I M, Tangen C M, Ankerst D P, Chi C, Lucia M S, Goodman P, et al. The performance of prostate specific antigen for predicting prostate cancer is maintained after a prior negative prostate biopsy. *J Urol.* 2008; 180(2):544-547.
27. Waters K M, Le Marchand L, Kolonel L N, Monroe K R, Stram D O, Henderson B E, et al. Generalizability of associations from prostate cancer genome-wide association studies in multiple populations. *Cancer Epidemiol Biomarkers Prev.* 2009; 18(4):1285-1289.
28. Kader A K, Sun J, Isaacs S D, Wiley K E, Yan G, Kim S T, et al. Individual and cumulative effect of prostate cancer risk-associated variants on clinicopathologic variables in 5,895 prostate cancer patients. *Prostate.* 2009; 69:1195-1205.
29. Fitzgerald L M, Kwon E M, Koopmeiners J S, Salinas C A, Stanford J L, Ostrander E A, et al. Analysis of recently identified prostate cancer susceptibility loci in a population-based study: associations with family history and clinical features. *Clin Cancer Res.* 2009; 15:3231-3237.
30. Marks L S, Fradet Y, Deras I L, Blase A, Mathis J, Aubin S M, et al. PCA3 molecular urine assay for prostate cancer in men undergoing repeat biopsy. *Urology.* 2007; 69(3): 532-535.

Example 7. Additional Description and Data

Background of the Problem that is Addressed.

Prostate cancer (PCa) is the most common solid organ malignancy affecting American men and the second leading cause of cancer related death. There are at least two major problems in diagnosing and preventing PCa: 1) it is difficult to predict men at elevated risk for PCa, and 2) it is difficult to predict outcome of prostate biopsy.

Recently, 33 PCa risk-associated single nucleotide polymorphisms (SNPs) have been identified. We assessed the ability of these 33 inherited PCa risk-associated genetic markers to address the problems listed above.

Brief Summary of the Invention.

Using clinical data and DNA samples from the REduction by DUtasteride of prostate Cancer Events (REDUCE) trial, we have obtained novel results that may have broad clinical utility:

a) Genetic score based on a panel of 33 PCa risk-associated SNPs (PCS33) can predict an individual's risk for PCa.

b) Genetic score based on PCS33 can supplement current clinical variables (PSA, prostate volume, age, and family history) to better determine the clinical decision to pursue prostate biopsy (or repeat prostate biopsy) for detection of PCa.

Description of a) Genetic score based on a panel of 33 PCa risk-associated SNPs (PC-S33) can predict individual risk for PCa, and b) Genetic score based on PC-S33 can supplement current clinical variables (PSA, prostate volume, age, and family history) to better determine the clinical decision to perform a prostate biopsy (or repeat prostate biopsy) for PCa detection. These were conceived prior to and confirmed using the population in the placebo arm of the REDUCE study.

Among the 1,654 men of European descent who had an initial negative biopsy for PCa and who consented to genetic study in the placebo arm of the REDUCE trial, 410 men (25%) had a positive prostate biopsy for PCa from scheduled and for-cause biopsies over the four-year study. In a univariate analysis (Table 5), men with positive biopsies had significantly higher genetic score based on PCS33 than men with negative prostate biopsy ($P=4.95\times10^{-9}$). After adjusting for known PCa risk-associated clinical variables such as age, free/total PSA ratio, number of cores at base biopsy, and prostate volume using multivariate logistic regression analysis, and family history, the genetic score remained significantly associated with positive prostate biopsy ($P=3.58\times10^{-8}$). The results from this prospective clinical trial establish the basis for the use of these genetic markers to predict an individual's risk for PCa.

We used the area under the receiver operating characteristic curve (AUC) to assess the performance of these baseline clinical variables and genetic score, individually and in combination, to predict for positive prostate biopsy during the four-year follow-up. To obtain unbiased estimates of AUC, a four-fold cross validation method was used and results from testing samples were reported (Table 6). The AUC of the genetic score was highest (0.59) among individual predictors; including prostate volume (0.56), age (0.56), number of cores sampled at pre-study entry biopsy (0.55), free/total PSA ratio (0.54), total PSA (0.54), family history (0.52), and DRE (0.51). When multiple predictors were included in the model simultaneously, the AUC for commonly used predictors including age, family history, and total PSA was 0.58. The best clinical model included five baseline variables (age, family history, free/total PSA ratio, number of cores at pre-study entry biopsy, and prostate volume), with an AUC of 0.60. When the genetic score was added to this best clinical model, the AUC of the full model increased to 0.64.

Figure 4:
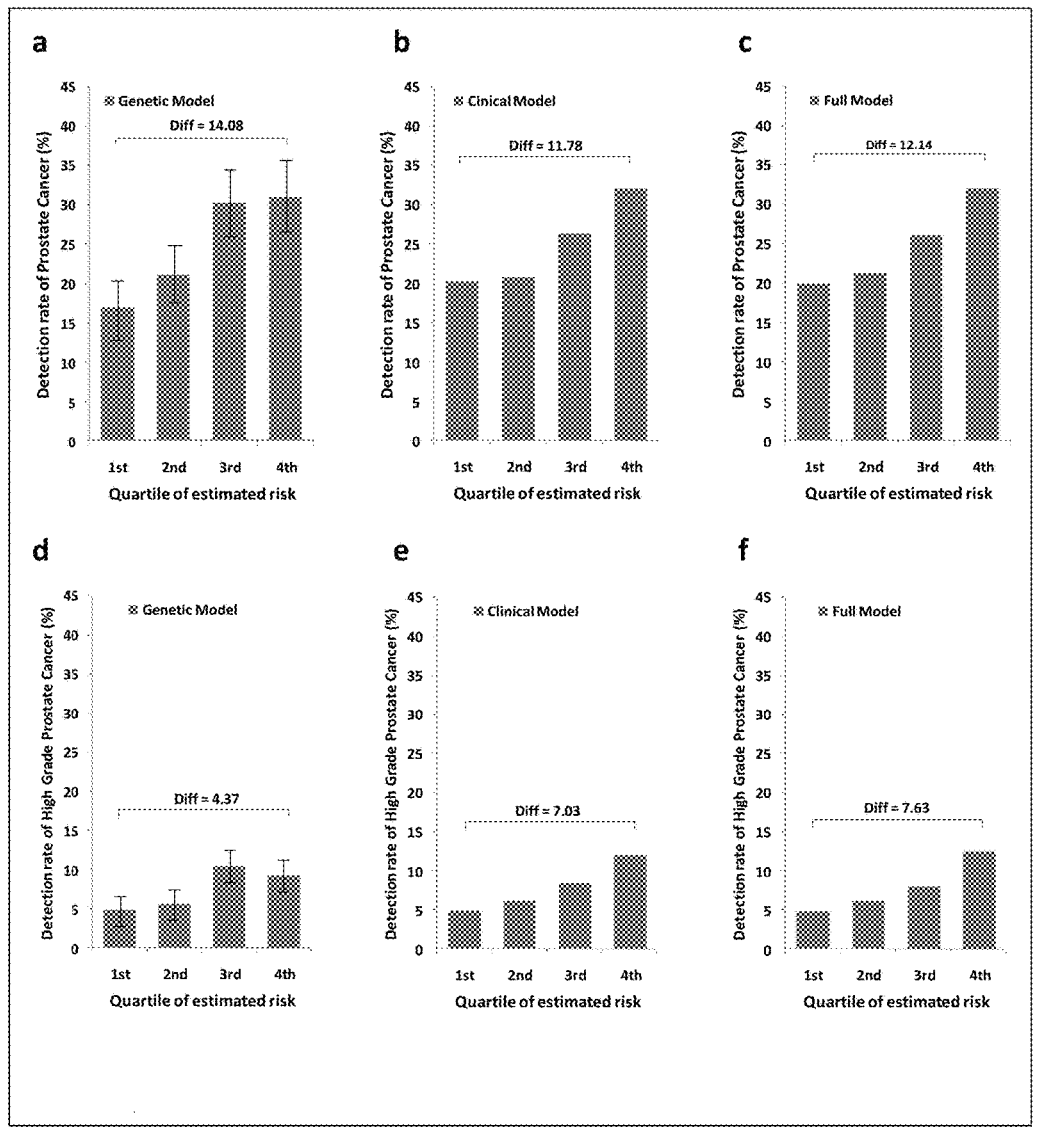
FIG. 4, panels a-f. Detection rate of PCa and high grade PCa among men with various estimated PCa risk based on genetic score, clinical variables and combination of both.

To facilitate the use and interpretation of these models in predicting positive prostate biopsy, we calculated the detection rate of PCa and high-grade PCa for the genetic score model, the best clinical model, and the full model (FIG. 4). For each model, the detection rate generally increased in men with increasingly higher estimated risk. The difference in PCa detection rate between the lowest and highest quartile was 14.08%, 11.78%, and 12.14% for the genetic score model, the best clinical model, and the full model that combined genetic score with the best clinical model, respectively (FIG. 4, panels a-c). The difference in high-grade PCa detection rate between the lowest and highest quartile was 4.37%, 7.03%, and 7.63% for the genetic model, the best clinical model, and the full model, respectively (FIG. 4, panels d-f).

Figure 5:
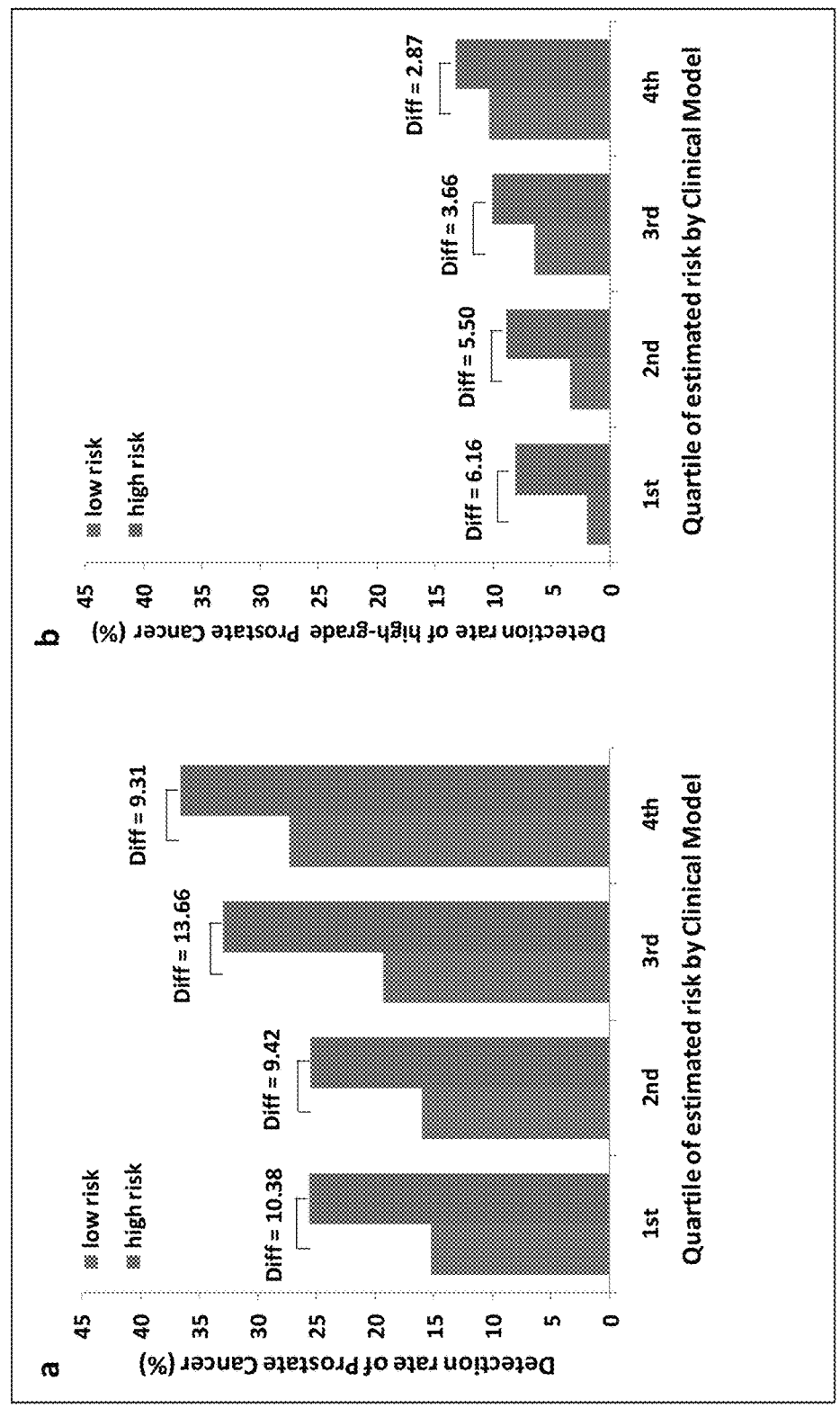
FIG. 5, panels a-b. Detection rate of PCa and high-grade PCa among men with various estimated PCa risk based on the best clinical variables, stratified by genetic risk.

To further examine the added value of the genetic score to the existing clinical parameters in predicting positive prostate biopsy, we estimated PCa detection rates in each quartile of risk based on the best clinical model, stratified by genetic score (lower and higher half) (FIG. 5, panel a). Within each clinical risk quartile, the detection rates differed considerably between men with lower and higher genetic scores; the difference was 10.38% in the 1st, 9.42% in the 2nd, 13.66% in the 3rd, and 9.31% in the 4th risk quartile, respectively. Comparing across the risk quartiles, men with higher genetic scores, even in the lower clinical risk quartile, had comparable or even higher PCa detection rate than men with lower genetic scores in any clinical risk quartile. Specifically, the PCa detection rate was 25.64% for men that had a higher genetic score within the lowest clinical risk quartile; this is comparable or higher than the detection rates among men that had a lower genetic score in the 2nd, 3rd, or highest clinical risk quartile (16.06%, 19.34%, and 27.34%, respectively). Similarly, genetic score was able to further differentiate the detection rate of high-grade PCa defined by the best clinical model (FIG. 5, panel b).

Through a direct comparison of the predictive performance (AUC) of the genetic score and existing clinical variables in the same study population, we showed that the genetic score performed better than any other individual clinical parameter, including PSA, for PCa risk prediction. More importantly, the genetic score improved the AUC of existing clinical variables. The strongest support for the added value of the genetic score to the existing clinical variables in this population is reflected by the ability of the genetic score to differentiate PCa detection rates among men in the same risk quartile defined by the best clinical model.

Prior to our study, it was not known whether reported PCa risk-associated SNPs are false positive due to PSA detection bias (i.e., these SNPs are associated with elevated PSA and not PCa risk per se, as elevated PSA leads to more prostate biopsies and in turn a greater PCa detection rate as is seen in case control studies). In addition, because many clinical variables such as PSA and DRE are commonly used to define cases and controls in case-control studies, it is difficult to assess relative predictive performance of genetic markers and clinical variables such as PSA, and more importantly whether genetic markers considerably improve the ability of existing clinical parameters to predict for PCa.

The placebo arm of the REDUCE study, a large randomized clinical trial, provided a unique opportunity to answer these questions. All men in the study had a negative biopsy at baseline and were followed-up for four years, with scheduled not-for-cause prostate biopsies at years 2 and 4. In addition, because it is a clinical trial, a number of clinical variables, such as free/total PSA ratio and prostate volume were measured at baseline using a standardized protocol. To our knowledge, our findings were the first to establish the clinical validity of these PCa risk-associated SNPs and the value they add to existing clinical variables for the prediction of PCa risk in a large prospective clinical trial.

On the basis of these studies, we have developed a genetic test using PCS33 to determine the need for prostate biopsy.

Example 8. Analysis of Randomly Selected Subsets of the 33 SNPs of Table 1

Calculations as described herein were performed on 10 and 15 randomly selected SNPs (Table 8) that are subsets of the 33 SNPs of Table 1 and this random sampling was repeated five times. The genetic scores (CRRs) calculated from these subsets is equivalent or better that the family history for detecting prostate cancer risk measured by AUC (Table 7).

The foregoing is illustrative of the present invention, and is not to be construed as limiting thereof. The invention is defined by the claims provided herein, with equivalents of the claims to be included therein.

All publications, patent applications, patents, patent publications, sequences identified by GenBank® Database accession numbers and/or SNP accession numbers, and other references cited herein are incorporated by reference in their entireties for the teachings relevant to the sentence and/or paragraph in which the reference is presented.

TABLE 1

Reported SNPs associated with PCa and their odds ratio from a meta-analysis

| CHR | SNPs | Note | BP-build36 | Known genes | m/M* allele | Risk allele | OR (95% CI) |
|---|---|---|---|---|---|---|---|
| 2 | rs1465618 | 2p21 | 43,407,453 | THADA | A/G | A | 1.15 (1.04-1.26) |
| 2 | rs721048 | 2p15 | 62,985,235 | EHBP1 | A/G | A | 1.16 (1.11-1.22) |

TABLE 1-continued

Reported SNPs associated with PCa and their odds ratio from a meta-analysis

| CHR | SNPs | Note | BP-build36 | Known genes | m/M* allele | Risk allele | OR (95% CI) |
|---|---|---|---|---|---|---|---|
| 2 | rs12621278 | 2q31.1 | 173,019,799 | ITGA6 | G/A | A | 1.35 (1.27-1.44) |
| 3 | rs2660753 | 3p12 | 87,193,364 | | T/C | T | 1.24 (1.04-1.48) |
| 3 | rs10934853 | 3q21.3 | 129,521,063 | | A/C | A | 1.12 (1.06-1.18) |
| 4 | rs17021918 | 4q22.3 | 95,781,900 | PDLIM5 | T/C | C | 1.14 (1.10-1.18) |
| 4 | rs7679673 | 4q24 | 106,280,983 | TET2 | A/C | C | 1.13 (1.10-1.17) |
| 6 | rs9364554 | 6q25 | 160,753,654 | | T/C | T | 1.17 (1.06-1.29) |
| 7 | rs10486567 | 7p15 | 27,943,088 | JAZF1 | A/G | G | 1.16 (1.10-1.23) |
| 7 | rs6465657 | 7q21 | 97,654,263 | LMTK2 | T/C | C | 1.14 (1.05-1.23) |
| 8 | rs2928679 | 8p21.2 | 23,494,920 | NKX3.1 | A/G | A | 1.13 (1.02-1.25) |
| 8 | rs1512268 | 8p21.2 | 23,582,408 | NKX3.1 | T/C | T | 1.17 (1.14-1.21) |
| 8 | rs10086908 | 8q24 (5) | 128,081,119 | | C/T | T | 1.13 (1.09-1.18) |
| 8 | rs16901979 | 8q24 (2) | 128,194,098 | | A/C | A | 1.80 (1.57-2.06) |
| 8 | rs16902094 | 8q24.21 | 128,389,528 | | N/A | G | 1.20 (1.12-1.30) |
| 8 | rs620861 | 8q24 (4) | 128,404,855 | | A/G | G | 1.16 (1.11-1.20) |
| 8 | rs6983267 | 8q24 (3) | 128,482,487 | | G/T | G | 1.20 (1.14-1.26) |
| 8 | rs1447295 | 8q24 (1) | 128,554,220 | | A/C | A | 1.47 (1.33-1.62) |
| 9 | rs1571801 | 9q33 | 123,467,194 | | G/A | A | 1.17 (0.95-1.45) |
| 10 | rs10993994 | 10q11 | 51,219,502 | MSMB | T/C | T | 1.25 (1.12-1.40) |
| 10 | rs4962416 | 10q26 | 126,686,862 | CTBP2 | C/T | C | 1.15 (1.04-1.27) |
| 11 | rs7127900 | 11P15.5 | 2,190,150 | IGF2, IGF2AS, INS, TH | G/A | A | 1.25 (1.20-1.30) |
| 11 | rs12418451 | 11q13 (2) | 68,691,995 | AL137479, BC043531 | A/G | A | 1.16 (1.09-1.23) |
| 11 | rs10896449 | 11q13 (1) | 68,751,243 | | A/G | G | 1.16 (1.11-1.22) |
| 17 | rs11649743 | 17q12 (2) | 33,149,092 | | A/G | G | 1.16 (1.11-1.22) |
| 17 | rs4430796 | 17q12 (1) | 33,172,153 | TCF2 | A/G | A | 1.22 (1.17-1.26) |
| 17 | rs1859962 | 17q24.3 | 66,620,348 | | G/T | G | 1.20 (1.13-1.27) |
| 19 | rs8102476 | 19q13.2 | 43,427,453 | | T/C | C | 1.12 (1.08-1.15) |
| 19 | rs887391 | 19q13 | 46,677,464 | 10 Mb to KLK3 | C/T | T | 1.14 (1.08-1.20) |
| 19 | rs2735839 | 19q13 (KLK3) | 56,056,435 | KLK3 | A/G | G | 1.30 (1.11-1.51) |
| 22 | rs9623117 | 22q13 | 38,782,065 | | C/T | C | 1.13 (1.05-1.22) |
| 22 | rs5759167 | 22q13.2 | 41,830,156 | TTLL1, BIK, MCAT, PACSIN2 | T/G | G | 1.18 (1.14-1.21) |
| 23 | rs5945619 | Xp11 | 51,258,412 | NUDT10, NUDT11, LOC340602 | C/T | C | 1.27 (1.12-1.43) |

*m = minor allele, M = major allele.

TABLE 2

Clinical and genetic predictors of prostate cancer

| Variables and models | Testing AUC from four-fold cross validation |
|---|---|
| Individual variables at baseline | |
| Age at baseline (Age) | 0.56 |
| Digital rectal examination at baseline (DRE) | 0.51 |
| Total PSA levels at baseline | 0.54 |
| Free/total PSA ratio at baseline (f/t PSA) | 0.54 |
| Prostate volume at baseline (PV) | 0.56 |
| Number of cores sampled at base biopsy (No. of cores) | 0.55 |
| Family history at baseline (FH) | 0.53 |
| Genetic score based on 33 PCa risk SNPs (Genetic score) | 0.59 |
| Combined variables | |
| Age + FH + total PSA | 0.58 |
| Age + FH + f/t PSA | 0.59 |
| Age + FH + DRE + f/t PSA | 0.59 |
| Age + FH + f/t PSA + PV + No. of cores | 0.60 |
| Age + FH + f/t PSA + PV + No. of cores + Genetic score | 0.64 |

TABLE 3

Baseline clinical, demographic, and genetic score of the subjects in the study

| | All subjects | | |
|---|---|---|---|
| Variables | Positive Biopsies | Negative Biopsies | P-values |
| Number of subjects | 410 | 1244 | |
| Age at baseline | | | |
| Mean (SD), years | 63.52 (5.99) | 62.22 (6.01) | 0.0001 |
| Range | 50-76 | 49-76 | |
| # (%) with positive family history at baseline | 68 (17%) | 146 (12%) | 0.01 |
| # (%) with positive DRE† at baseline | 20 (5%) | 47 (4%) | 0.33 |
| Total PSA levels at baseline | | | |
| Mean (SD), mL | 5.78 (1.37) | 5.52 (1.40) | 0.01 |
| Range, mL | 2.5-10.2 | 1.8-14.2 | |
| Free/total PSA ratio at baseline | 0.16 (0.06) | 0.17 (0.06) | 0.02 |
| Prostate volume at baseline | 44.20 (21.40) | 46.76 (16.13) | 0.03 |
| Number of cores sampled at base biopsy | 8.21 (2.27) | 8.58 (2.39) | 0.004 |
| Genetic score based on 33 PCa risk SNPs | 0.94 (1.83) | 0.77 (1.81) | 4.95E−09 |

†DRE: Digital rectal examination

TABLE 4

Comparison of characteristics for men in the placebo group consented or declined genetic studies

| | Consented for genetic studies | | |
|---|---|---|---|
| Variables | Yes | No | P-values |
| Number of subjects | 1654 | 1475 | |
| Age at baseline | | | |
| Mean (SD), years | 62.55 (6.03) | 62.87 (6.03) | 0.13 |
| Range | 49-76 | 49-77 | |
| # (%) with positive family history at baseline | 214 (12.94) | 188 (12.75) | 0.87 |
| # (%) with positive DRE† at baseline | 67 (4.06) | 51 (3.47) | 0.39 |
| Total PSA levels at baseline | | | |
| Mean (SD), mL | 5.89 (1.89) | 5.98 (1.97) | 0.18 |
| Range, mL | 1.8-14.2 | 2.4-23.2 | |
| Free/total PSA ratio at baseline | | | |
| Mean (SD), mL | 0.16 (0.06) | 0.17 (0.06) | 0.02 |
| Range, mL | 0.03-0.47 | 0.04-0.64 | |
| Prostate volume at baseline | | | |
| Mean (SD), mL | 46.13 (17.62) | 44.58 (17.61) | 0.02 |
| Range, mL | 3.66-256.83 | 5.75-264.94 | |

†DRE: Digital rectal examination

TABLE 5

Baseline clinical, demographic, and genetic score of the subjects in the study

| | All subjects | | | Subjects with positive Biopsies | | |
|---|---|---|---|---|---|---|
| Variables | Positive Biopsies | Negative Biopsies | P-values | Gleason grade ≤6 | Gleason grade ≥7 | P-values |
| Number of subjects | 410 | 1244 | | 286 | 124 | |
| Age at baseline | | | | | | |
| Mean (SD), years | 63.52 (5.99) | 62.22 (6.01) | 0.0001 | 63.01 (6.02) | 64.72 (5.75) | 0.008 |
| Range | 50-76 | 49-76 | | 50-76 | 52-75 | |
| # (%) with positive family history at baseline | 68 (17%) | 146 (12%) | 0.01 | 44 (15%) | 24 (19%) | 0.32 |
| # (%) with positive DRE† at baseline | 20 (5%) | 47 (4%) | 0.33 | 15 (5%) | 5 (4%) | 0.60 |
| Total PSA levels at baseline | | | | | | |
| Mean (SD), mL | 5.78 (1.37) | 5.52 (1.40) | 0.01 | 5.62 (1.37) | 6.16 (1.36) | 0.008 |
| Range, mL | 2.5-10.2 | 1.8-14.2 | | 2.5-10.2 | 2.7-10 | |
| Free/total PSA ratio at baseline | 0.16 (0.06) | 0.17 (0.06) | 0.02 | 0.16 (0.06) | 0.15 (0.07) | 0.32 |
| Prostate volume at baseline | 44.20 (21.40) | 46.76 (16.13) | 0.03 | 45.29 (22.54) | 41.72 (18.38) | 0.10 |
| Number of cores sampled at base biopsy | 8.21 (2.27) | 8.58 (2.39) | 0.004 | 8.30 (2.15) | 8.00 (2.51) | 0.09 |
| Genetic score based on 33 PCa risk SNPs | 0.94 (1.83) | 0.77 (1.81) | 4.95E−09 | 0.93 (1.84) | 0.96 (1.80) | 0.66 |

†DRE: Digital rectal examination

TABLE 6

Clinical and genetic predictors of prostate cancer and high-grade prostate cancer

| | Testing AUC from four-fold cross validation | |
|---|---|---|
| Variables and models | Any prostate cancer | High-grade prostate cancer |
| Individual variables at baseline | | |
| Age at baseline (Age) | 0.56 | 0.61 |
| Digital rectal examination at baseline (DRE) | 0.51 | 0.50 |
| Total PSA levels at baseline | 0.54 | 0.59 |
| Free/total PSA ratio at baseline (f/t PSA) | 0.54 | 0.57 |
| Prostate volume at baseline (PV) | 0.56 | 0.59 |
| Number of cores sampled at base biopsy (No. of cores) | 0.55 | 0.58 |
| Family history at baseline (FH) | 0.53 | 0.54 |
| Genetic score based on 33 PCa risk SNPs (Genetic score) | 0.59 | 0.57 |
| Combined variables | | |
| Age + FH + total PSA | 0.58 | 0.65 |
| Age + FH + f/t PSA | 0.59 | 0.65 |
| Age + FH + DRE + f/t PSA | 0.59 | 0.65 |
| Age + FH + f/t PSA + PV + No. of cores | 0.60 | 0.67 |
| Age + FH + f/t PSA + PV + No. of cores + Genetic score | 0.64 | 0.67 |

High-grade prostate cancer is defined as Gleason grade 7 or higher

TABLE 7

| | Random sample 1 | Random sample 2 | Random sample 3 | Random sample 4 | Random sample 5 |
|---|---|---|---|---|---|
| FH | 0.53 | | | | |
| GS33 | 0.59 | | | | |
| GS15 | | 0.56 | 0.55 | 0.56 | 0.53 | 0.55 |
| GS10 | | 0.54 | 0.54 | 0.54 | 0.56 | 0.53 |

TABLE 8

|  | Random Sample 1 | Random Sample 2 | Random Sample 3 | Random Sample 4 | Random Sample 5 |
|---|---|---|---|---|---|
| 15 SNPs | rs1465618 | rs1465618 | rs10934853 | rs721048 | rs1465618 |
|  | rs12621278 | rs721048 | rs17021918 | rs12621278 | rs721048 |
|  | rs7679673 | rs12621278 | rs10486567 | rs2660753 | rs12621278 |
|  | rs6465657 | rs17021918 | rs6465657 | rs17021918 | rs10934853 |
|  | rs2928679 | rs7679673 | rs2928679 | rs7679673 | rs2928679 |
|  | rs1512268 | rs9364554 | rs1512268 | rs9364554 | rs10086908 |
|  | rs16901979 | rs6465657 | rs16901979 | rs10486567 | rs620861 |
|  | rs620861 | rs10086908 | rs620861 | rs2928679 | rs7127900 |
|  | rs10993994 | rs16902094 | rs10993994 | rs10086908 | rs12418451 |
|  | rs7127900 | rs620861 | rs7127900 | rs6983267 | rs11649743 |
|  | rs12418451 | rs11649743 | rs12418451 | rs4962416 | rs4430796 |
|  | rs11649743 | rs1859962 | rs8102476 | rs7127900 | rs1859962 |
|  | rs4430796 | rs2735839 | rs887391 | rs12418451 | rs8102476 |
|  | rs2735839 | rs9623117 | rs9623117 | rs11649743 | rs9623117 |
|  | rs5945619 | rs5759167 | rs5945619 | rs887391 | rs5759167 |
| 10 SNPs | rs17021918 | rs1465618 | rs1465618 | rs1465618 | rs1465618 |
|  | rs9364554 | rs12621278 | rs12621278 | rs10934853 | rs12621278 |
|  | rs6465657 | rs10934853 | rs1512268 | rs6465657 | rs7679673 |
|  | rs2928679 | rs9364554 | rs16901979 | rs2928679 | rs6465657 |
|  | rs1512268 | rs10486567 | rs1571801 | rs1512268 | rs1571801 |
|  | rs16901979 | rs10086908 | rs10993994 | rs10086908 | rs7127900 |
|  | rs1571801 | rs620861 | rs12418451 | rs6983267 | rs8102476 |
|  | rs11649743 | rs6983267 | rs11649743 | rs12418451 | rs9623117 |
|  | rs1859962 | rs1571801 | rs9623117 | rs11649743 | rs5759167 |
|  | rs9623117 | rs7127900 | rs5759167 | rs1859962 | rs5945619 |

What is claimed is:

1. A method of performing a prostate biopsy on a subject comprising:
   a) obtaining a nucleic acid sample from the subject;
   b) assaying the nucleic acid sample obtained from the subject, and detecting a genotype for the subject at a plurality of biallelic polymorphic loci, wherein the allele present is detected for both copies of each biallelic polymorphic loci, and wherein the plurality of biallelic polymorphic loci consists of the SNPs rs1465618, rs10934853, rs6465657, rs2928679, rs1512268, rs10086908, rs6983267, rs12418451, rs11649743, and rs1859962, and optionally any one or more SNP selected from the group consisting of rs721048, rs12621278, rs2660753, rs17021918, rs7679673, rs9364554, rs10486567, rs16901979, rs16902094, rs620861, rs1447295, rs1571801, rs10993994, rs4962416, rs7127900, rs10896449, rs4430796, rs8102476, rs887391, rs2735839, rs9623117, rs5759167, and rs5945619;
   c) calculating the cumulative relative risk for the subject based on the genotypes detected in (b);
   d) identifying the subject as having a cumulative relative risk that is greater than the average population risk; and
   e) performing the prostate biopsy on the subject.

2. The method of claim 1, wherein the subject has a family history of prostate cancer.

3. The method of claim 1, wherein the subject has a prior negative prostate biopsy.

4. The method of claim 1, wherein the subject has no family history of prostate cancer.

5. A method of administering dutasteride or finasteride to a subject comprising:
   a) obtaining a nucleic acid sample from the subject;
   b) assaying the nucleic acid sample obtained from the subject, and detecting a genotype for the subject at a plurality of biallelic polymorphic loci, wherein the allele present is detected for both copies of each polymorphic loci, and wherein the plurality of biallelic polymorphic loci consists of the SNPs rs1465618, rs10934853, rs6465657, rs2928679, rs1512268, rs10086908, rs6983267, rs12418451, rs11649743, and rs1859962, and optionally any one or more SNP selected from the group consisting of rs721048, rs12621278, rs2660753, rs17021918, rs7679673, rs9364554, rs10486567, rs16901979, rs16902094, rs620861, rs1447295, rs1571801, rs10993994, rs4962416, rs7127900, rs10896449, rs4430796, rs8102476, rs887391, rs2735839, rs9623117, rs5759167, and rs5945619;
   c) calculating the cumulative relative risk for the subject based on the genotypes detected in (b);
   d) identifying the subject as having a cumulative relative risk that is greater than the average population risk; and
   e) administering dutasteride or finasteride to the subject.

6. The method of claim 5, wherein the subject has a family history of prostate cancer.

7. The method of claim 5, wherein the subject has a prior negative prostate biopsy.

8. The method of claim 5, wherein the subject has no family history of prostate cancer.

9. A method of measuring a prostate serum antigen (PSA) level in a subject comprising:
   a) obtaining a nucleic acid sample from the subject;
   b) assaying the nucleic acid sample obtained from the subject, and detecting a genotype for the subject at a plurality of biallelic polymorphic loci, wherein the allele present is detected for both copies of each polymorphic loci, and wherein the plurality of biallelic polymorphic loci consists of the SNPs rs1465618, rs10934853, rs6465657, rs2928679, rs1512268, rs10086908, rs6983267, rs12418451, rs11649743, and rs1859962, and optionally any one or more SNP selected from the group consisting of rs721048, rs12621278, rs2660753, rs17021918, rs7679673, rs9364554, rs10486567, rs16901979, rs16902094, rs620861, rs1447295, rs1571801, rs10993994, rs4962416, rs7127900, rs10896449, rs4430796, rs8102476, rs887391, rs2735839, rs9623117, rs5759167, and rs5945619;

c) calculating the cumulative relative risk for the subject based on the genotypes detected in (b);
d) identifying the subject as having a cumulative relative risk that is greater than the average population risk; and
e) measuring the PSA level in the subject.

10. The method of claim 9, wherein the subject has a family history of prostate cancer.

11. The method of claim 9, wherein the subject has a prior negative prostate biopsy.

12. The method of claim 9, wherein the subject is under 50 years old.

13. The method of claim 9, wherein the subject has no family history of prostate cancer.

* * * * *